US009682197B2

(12) United States Patent
Eaton et al.

(10) Patent No.: US 9,682,197 B2
(45) Date of Patent: Jun. 20, 2017

(54) SYSTEMS AND METHODS FOR PERFORMING AN INJECTION

(75) Inventors: Alexander M. Eaton, Fort Myers, FL (US); Dyson Hickingbotham, Wake Forest, NC (US); David Booth, Reading, PA (US); Gabriel Gordon, Santa Barbara, CA (US)

(73) Assignee: ITECH JV DEVELOPMENT COMPANY, LLC, Fort Myers, FL (US)

( * ) Notice: Subject to any disclaimer, the term of this patent is extended or adjusted under 35 U.S.C. 154(b) by 57 days.

(21) Appl. No.: 14/240,336

(22) PCT Filed: Aug. 23, 2012

(86) PCT No.: PCT/US2012/052174
§ 371 (c)(1),
(2), (4) Date: Feb. 21, 2014

(87) PCT Pub. No.: WO2013/028936
PCT Pub. Date: Feb. 28, 2013

(65) Prior Publication Data
US 2014/0221970 A1     Aug. 7, 2014

Related U.S. Application Data

(60) Provisional application No. 61/526,558, filed on Aug. 23, 2011, provisional application No. 61/598,865, (Continued)

(51) Int. Cl.
*A61M 5/32*     (2006.01)
*A61J 1/20*     (2006.01)
(Continued)

(52) U.S. Cl.
CPC ......... *A61M 5/3257* (2013.01); *A61F 9/0026* (2013.01); *A61J 1/2096* (2013.01);
(Continued)

(58) Field of Classification Search
CPC .............. A61M 5/3257; A61M 5/3273; A61M 2005/3258; A61M 2005/3267; A61F 9/0026; A61F 9/0008
See application file for complete search history.

(56) References Cited

U.S. PATENT DOCUMENTS 3,134,380 A * 5/1964 Armao .................. A61M 5/001
604/198
3,406,687 A * 10/1968 Moyer ................ A61M 5/3243
604/117
(Continued)

FOREIGN PATENT DOCUMENTS

WO     WO-2004/000397 A1     12/2003

OTHER PUBLICATIONS

Needle Gauge Comparison Chart, Wikipedia, accessed Dec. 21, 2015.*

(Continued)

*Primary Examiner* — Andrew Gilbert
(74) *Attorney, Agent, or Firm* — Mintz Levin Cohn Ferris Glovsky and Popeo, P.C.

(57) ABSTRACT

Devices, systems, and methods for performing injections with lowered likelihood of infection include needles and other injection means with protective sleeves or sheaths. The protective sleeve can protect the needle before, during, or before and during an injection. The force needed to administer an injection or penetrate an insertion site using an injection device or system with a protective sleeve can be about the same to up to 50% more than the force needed for a system or device without a protective sleeve. The force needed to collapse the protective sleeve can be less than 100 gram-force. The material, the thickness, or both the material and the thickness of the protective sleeve may differ when (Continued)

comparing the portion of the sleeve near the needle tip and the portion near the base of the needle.

31 Claims, 20 Drawing Sheets

Related U.S. Application Data filed on Feb. 14, 2012, provisional application No. 61/643,138, filed on May 4, 2012.

(51) Int. Cl.
    *A61M 5/178*      (2006.01)
    *A61F 9/00*      (2006.01)

(52) U.S. Cl.
    CPC ......... *A61M 5/3202* (2013.01); *A61F 9/0008* (2013.01); *A61M 5/1782* (2013.01); *A61M 2005/3258* (2013.01); *A61M 2005/3267* (2013.01); *A61M 2205/02* (2013.01); *A61M 2205/19* (2013.01); *A61M 2210/00* (2013.01); *A61M 2210/0612* (2013.01)

(56) References Cited

U.S. PATENT DOCUMENTS

| | | | |
|---|---|---|---|
| 3,703,174 A | | 11/1972 | Smith |
| 3,867,937 A | * | 2/1975 | Schwartz ............ A61M 25/0111 604/164.09 |
| 4,775,369 A | * | 10/1988 | Schwartz .............. A61M 5/326 604/198 |
| 4,795,432 A | * | 1/1989 | Karczmer ............ A61M 5/3257 604/110 |
| 4,846,809 A | * | 7/1989 | Sims .................... A61M 5/326 604/198 |
| 5,290,254 A | * | 3/1994 | Vaillancourt ........ A61B 5/1438 128/919 |
| 5,356,387 A | * | 10/1994 | Sirbola ............... A61M 5/3275 604/198 |
| 5,360,408 A | | 11/1994 | Vaillancourt |
| 5,658,256 A | * | 8/1997 | Shields ............... A61M 5/3202 604/192 |
| 6,159,175 A | | 12/2000 | Strukel et al. |
| 6,238,371 B1 | * | 5/2001 | Himbert ................ A61M 5/326 604/187 |
| 2007/0190058 A1 | | 8/2007 | Shams |
| 2009/0069712 A1 | * | 3/2009 | Mulvihill ............ A61B 10/025 600/564 |
| 2010/0030150 A1 | * | 2/2010 | Paques ................ A61F 9/0017 604/116 |
| 2010/0100054 A1 | * | 4/2010 | Cormier ............... A61F 9/0017 604/239 |
| 2010/0152646 A1 | * | 6/2010 | Girijavallabhan .... A61F 9/0017 604/22 |
| 2010/0318034 A1 | | 12/2010 | Goncalves |
| 2011/0071492 A1 | * | 3/2011 | Horvath ................ A61M 5/326 604/506 |
| 2012/0078224 A1 | * | 3/2012 | Lerner .................. A61F 9/0017 604/506 |

OTHER PUBLICATIONS

International Search Report and Written Opinion Issued in PCT/US2012/052174 dated Nov. 16, 2012.

* cited by examiner

SYSTEMS AND METHODS FOR PERFORMING AN INJECTION

This application is a national stage filing of PCT Patent Application No. PCT/US2012/052174, filed Aug. 23, 2012, titled "SYSTEMS AND METHODS FOR PERFORMING AN INJECTION," which in turn claims priority to the following three applications: U.S. Provisional Application No. 61/643,138, filed May 4, 2012, titled "SYSTEMS AND METHODS FOR PERFORMING AN INJECTION," U.S. Provisional Application No. 61/598,865, filed Feb. 14, 2012, titled "SYSTEMS AND METHODS FOR PERFORMING AN INJECTION," and U.S. Provisional Application No. 61/526,558, filed Aug. 23, 2011, titled "SYSTEMS AND METHODS FOR PERFORMING AN INJECTION." The priority of Aug. 23, 2011 is claimed and the disclosure of each of the aforementioned applications is hereby incorporated by reference in their entirety herein.

TECHNICAL FIELD

Some embodiments of the current subject matter generally relate to the field of injections. In particular, the current subject matter relates to injection devices, systems, and methods configured to prevent or substantially diminish occurrence of an infection during and/or after an injection.

BACKGROUND

An injection is an infusion method of putting fluid into the body, usually with a hollow needle and a syringe which is pierced through the skin to a sufficient depth for the material to be forced into the body. There are several methods of injection or infusion, including intradermal, subcutaneous, intramuscular, intravenous, intraosseous, intraperitoneal, and intraocular. Injections are among the most common health care procedures, with several billion administered each year. 95% of injections are administered in curative care, 3% for immunization and the rest for other purposes, such as blood transfusions. Some types of injections, such as intraocular injections, may benefit from the use of various devices to assist a medical professional (e.g., a doctor, a surgeon, a nurse, a medical technician, etc.) performing the injection. These devices are typically used to allow uninterrupted injection into a designated injection location. In case of intraocular injections, eyelid speculum(s) can be used to prevent a patient from blinking and interfering with the injection into the patient's eye.

Injections can be performed using a syringe-type device (which can include a hollow reservoir for containing an injection fluid and having a plunger configured to (via application of an external force) push the injection fluid through a needle coupled to the hollow reservoir and into the injection site), a catheter-type device, or any other device and can involve a penetration of a surface (e.g., skin, membranes, etc.) at the site of the injection. In view of such penetration, some injections can carry a risk of an infection either during and/or after the injection. For example, an intraocular injection of fluid can carry a risk of an intraocular infection after the injection through contamination of a needle used to perform such injection.

In 2008, over 1,017,000 intravitreal ("IV") injections were given to patients, which are up from 533,000 injections in 2007. This number has been increasing in recent years due in large part to the effectiveness of injection drugs, such as AVASTIN®, LUCENTIS® and most recently Eylea®. Many studies have been performed looking at the incidence of infection following these IV injections and the average incidence has been found to be approximately 0.05%, though this can range anywhere from 0% to 1% depending on the study. While this is a small fraction of the total, the outcomes for patients who develop some form of intraocular infection is usually not good and commonly results in a significant and permanent loss of vision.

As part of an injection procedure when the medication does not come in a prefilled syringe, the medication needs to be drawn up from a vial containing the drug. These vials can come in various sizes and shapes, and typically have a rubber like stopper attached to the top of the bottle. The drug is typically drawn up with a needle that is attached to a syringe. In some cases the needle will have a filter inside it to prevent any of the stopper or other contaminants from getting into the syringe and being injected. The needle used to draw up the drug is then typically discarded, and a new needle is placed on the syringe for injection of the drug/medication.

While there are covered needles in use today, such as the ones used in combination with vacutainers, they are not practical for direct use with patients or drug filled containers. They are one piece, opaque, and require significant force in order to displace them. They lack the features ideal for injections into humans or animals. Such features would include the means to minimize the forces required to keep them safe, and to minimize discomfort. Visualization of the needle is also preferred so its location is known at all times, which is achieved through the use of transparent or clear plastics or materials in most cases. Addition of color to the clear plastic so that a transparent colored sleeve can be helpful to enhance visualization of the sleeve over or next to human or animal tissue. It is also preferable to keep the materials thin, so that they do not interfere with other devices that reduce the risk of needle stick to health care personnel.

Hence, there is a need for a system, a method, and/or a device configured to reduce the incidence of contamination when a drug is drawn up and infection during the injection into tissue. Such injection system, method, and/or device can also be configured to reduce and/or eliminate a need for an injection assistance device such as a lid speculum to hold the lids open in the case of an intraocular injection, as well as protect sterility of an injection device's components (e.g., a needle). These can also be configured to increase patient comfort during and/or after an injection and to protect needles from causing or spreading infections in other areas such as intravenous tubing or other medical devices as well as to help insure proper placement of the needle for insertion into an injection site relative to another structure near the injection site.

SUMMARY

In some embodiments, the current subject matter relates to a device that includes a sleeve that surrounds a needle at a distal end of an injection device, in which the sleeve covers the needle, at least partially, before and during the penetration of the needle into an insertion site. In such embodiments, a force of less than 100 gram-force is required to collapse the sleeve.

The device can include any of the following features in any suitable combination. In some embodiments, the sleeve of the device may not penetrate the insertion site. In some embodiments of the device, the force required to collapse the sleeve can be determined by calculating the amount of force needed to insert the needle when using the needle with the sleeve and subtracting the amount of force needed to insert the needle in a similar manner without the sleeve. Alternatively, in some embodiments, the force required to collapse the sleeve can be measured by advancing a needle with a protective sleeve into a simulated human sclera at a rate of 100 microns per second until up to 70% of the portion of the sleeve that is capable of collapse has collapsed. In some such embodiments, the force required to collapse the sleeve can be measured by advancing a needle with a protective sleeve into a simulated human sclera at a rate of 100 microns per second until up to 30% of the portion of the sleeve that is capable of collapse has collapsed. Additionally, in some embodiments, the device can be one in which the needle includes a tip at its distal end, in which the sleeve includes a contamination prevention tip located at the distal end of the sleeve surrounding needle tip, the contamination prevention tip not being part of the portion of the sleeve that is capable of collapse. In some embodiments of the device, the force required to collapse the sleeve can range from 0.0001 gram-force to 100 gram-force. Additionally, the force required to collapse the sleeve can range from 0.0001 gram-force to 75 gram-force. In some embodiments, the sleeve can be clear or transparent. The sleeve can also include color pigments so as to allow easier visualization of the sleeve, and the sleeve can be sufficiently transparent to allow visualization of the needle. In some embodiments of the device, the needle can have an outside diameter and the sleeve can have an inside diameter such that the difference between the needle's outside diameter and sleeve's inside diameter is between 0.05 and 6 times the diameter of the needle. In such embodiments, the difference between the needle's outside diameter and sleeve's inside diameter can be based upon the smallest inside diameter of the sleeve and the average outside diameter of the needle. In some embodiments, the device can have a sleeve in which the sleeve has an enlarged portion of the sleeve adjacent to the needle tip. In such embodiments, the enlargement can be achieved by attaching a piece of tubing that is larger than the sleeve covering the needle only at a portion of the sleeve adjacent to the needle tip. Additionally, in such embodiments, the enlargement can be achieved by attaching a piece of tubing inside the sleeve that covers the needle only at a portion of the sleeve adjacent to the needle tip. In such embodiments in which the device has a sleeve with an enlarged portion adjacent to the needle tip, the sleeve can have a thickness of 0.0020 inches or less and the enlarged portion of the sleeve has a thickness of 0.0100 inches or more. In some embodiments, the device can have a sleeve with an enlarged portion adjacent to the needle tip in which the enlarged portion of the sleeve has a length less than or equal to ½ the length of the sleeve. In some embodiments of the device, the sleeve can have a baffle configuration that allows for a controlled collapse. The sleeve can further include an antibacterial, an antifungal medication, an antiprotozoal, or anti-microbial medication or agent. In such embodiments in which the sleeve includes an antibacterial, an antifungal medication, an antiprotozoal, or anti-microbial medication or agent, an agent can include colloidal silver or any other suitable form of silver, colloidal gold, antimicrobial chemicals, or any other substance that kills or inhibits the growth of viruses or microorganisms including bacteria, fungi, or protozoans. In some embodiments, the device can include an offset marker at the distal end of the sleeve. In such embodiments, the offset marker can include hash marks, variations in coloring, variations in size or any combination thereof that indicate increments of distance. The offset marker can be straight, curved, looped, a ring, a rectangle, or any combination thereof. Additionally, the offset marker can be angled forward, backward or at a 90° from the needle axis. In some embodiments in which the device can include an offset marker, the offset marker can be rigid or resilient. Alternatively, the offset marker can be flexible. In some embodiments, the sleeve can include plastic, silicone, medical grade silicone, Polyethelene (PE), TetraFluorEthylene-Perfluorpropylene (FEP), PerFluoroAlkoxy (PFA), or any combination thereof. In some embodiments, an additional force needed to collapse the sleeve can be defined as the difference between: the force need to penetrate a first injection site using the needle with the sleeve and the force needed to penetrate a second injection site using the needle without the sleeve over the force needed to penetrate the first injection site using the needle without the sleeve expressed as a percentage, in which the first and second injection sites include similar tissue or material, and also in which the additional force needed to collapse the sleeve can be less than 50% of the force need to insert the needle without the sleeve. In some such embodiments, the additional force needed to collapse the sleeve can be less than 25% of the force need to insert the needle without the sleeve. In some such embodiments, forces needed to derive the additional force need to collapse the sleeve can include the force needed to penetrate the first injection site using the needle with the sleeve and the force needed to penetrate the second injection site using the needle without the sleeve. In such embodiments, the forces needed to derive the additional force needed to collapse the sleeve can be measured by advancing the needle with and without the protective sleeve into a simulated human sclera at a rate of 100 microns per second until up to 70% of the portion of the sleeve that is capable of collapse has collapsed.

In some embodiments, the current subject matter relates to a method of treating an eye that includes providing a device that includes an injection device that includes an injection needle, a fluid to be injected into the eye, and a sleeve that is configured to at least partially cover the injection needle before and during an injection. The injection needle includes a distal section configured to penetrate an injection site. The fluid to be injected into the eye is disposed within the injection device. The method further includes introducing the distal section of the injection needle into the eye, advancing the distal section of the injection needle into a tissue, cavity, gel filled site, fluid filled site, or a gel and tissue filled site inside the eye, and injecting the fluid into the eye while protecting the needle from being contacted by an eyelid, aerosolized contaminants, spit or other contaminants.

The method of treating an eye can include any of the following features in any suitable combination. In some embodiments, the fluid can include a liquid, a gas, a gel, a medication, or any combination thereof. In some embodiments, the site inside the eye can include a tissue site, a cavity, a gel filled site, a fluid filled site, or a gel and tissue filled site. In some embodiments, the sleeve can remain outside of the eye while introducing the distal section of the injection needle into the eye. In some embodiments, the fluid can be injected into the eye without the aid of a device to hold the eyelid open. Alternatively, in some embodiments, the fluid can be injected into the eye with the aid of a device to hold the eyelid open.

In some embodiments, the current subject matter relates to a method that includes providing an apparatus that includes a needle that has a distal section and is configured to penetrate the top of a vial or container, a fluid to be drawn up from or injected into the vial or container, and a sleeve that is configured to at least partially cover the needle before and during introducing the distal section of the needle in the vial or container. The method further include injecting the fluid or drawing the fluid up from the vial or container into or out of a syringe or injection device while protecting the needle from being contacted by skin, touch, spit, or other aerosolized or contact contaminants.

The method can include any of the following features in any suitable combination. In some embodiments, the fluid can include a liquid, a gas, a gel, a medication, or any combination thereof. In some embodiments, the needle can further include a filter to eliminate particulate matter from being drawn up with the fluid from the vial or container. In some embodiments, the fluid can include a medication, a gas, or both a medication and a gas.

In some embodiments, the current subject matter relates to a method that includes providing an apparatus that includes a needle with a distal section, configured to penetrate an injection site; a fluid to be injected into the injection site; and a sleeve, wherein the sleeve is configured to at least partially cover the needle before and during introducing the distal section of the needle into the injection site. The method also includes advancing the distal section of the needle into the injection site and injecting a fluid out of a syringe or injection device while protecting the needle from being contacted by skin, touch, spit, or other aerosolized or contact contaminants.

In some embodiments, the current subject matter relates to an injection device that includes a needle and a retractable sleeve movable on application of a force less than 100 gram-force from an initial position in which the sleeve covers the entire needle to a second position in which at least a portion of the sleeve is collapsed and at least a portion of the needle is not covered beyond the tip of the sleeve.

In other embodiments, the current subject matter relates to an injection device that includes a needle and a sleeve that surrounds the needle in an initial configuration, but the sleeve collapses to expose at least a portion of the needle beyond a tip of the sleeve upon application of a force less than 100 gram-force.

BRIEF DESCRIPTION OF THE DRAWINGS

The current subject matter is described with reference to the accompanying drawings. In the drawings, like reference numbers indicate identical or functionally similar elements. Additionally, the left-most digit(s) of a reference number identifies the drawing in which the reference number first appears.

DETAILED DESCRIPTION

Figure 1:
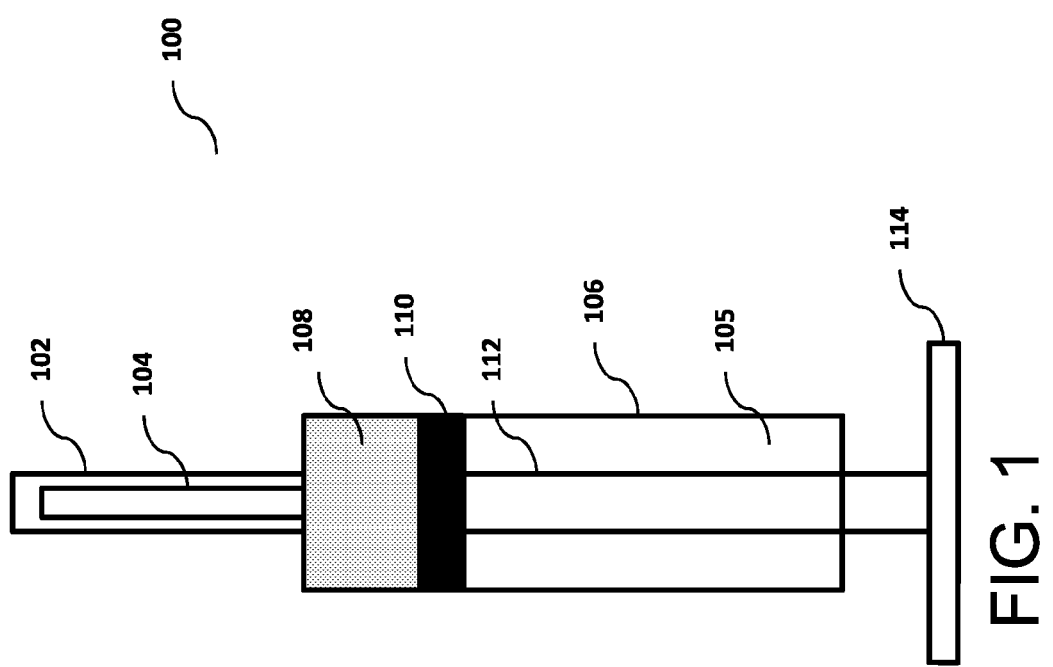
FIG. 1 illustrates an exemplary injection device prior to performing an injection, according to some embodiments of the current subject matter.

As stated above, some embodiments of the current subject matter relates to injection devices, systems, and/or methods configured to prevent and/or substantially reduce occurrence of an infection during and/or after an injection. Additionally, some embodiments also allow for the accurate placement of an injection needle relative to an anatomical or physical structure in terms of surface location, as well as depth, using only the injection devices described herein. Some embodiments allow for increased comfort of a patient while mitigating infection by providing an injection system and/or methods which can be used without added instrumentation during an injection.

The needles used in the devices, systems, and methods described herein are generally made of metals, such as stainless steel (303, 304, 316, or 400 series (e.g. 420)), titanium, or such other metals or alloys, but can also be made out of plastic, glass or ceramic materials depending on the application. The needles used in the devices, systems, and methods described herein can be straight, curved, angled, or have any geometry necessary to effectively penetrate an insertion site or apply an injection or infusion.

In some embodiments, a sleeve may be used to cover a metal or plastic needle that is used to inject fluids, medications or other materials into IV tubing, butterfly needles, parenteral nutrition tubing, respiratory tubing, urinary, cerebral spinal fluid or any other medical tubing used to deliver fluids or materials to human or animals. A sleeve can also be used to cover needles on catheters that are used for intravenous, intra-arterial, abdominal, renal, central nervous system or any other access.

In some embodiments, a needle and sleeve system or device can be used in a method of drawing up a fluid, such as a liquid, a liquid that include a medication, a gel, a suspension that includes a medication, a gel that includes a medication, a colloidal suspension, a microsphere containing a medication, a medication, and/or gas, or any other injectable medical therapy, from a vial. The vial may be glass, with a rubber stopper. The method may include providing an apparatus which includes: a needle with a distal section that is also configured to penetrate the rubber stopper of a fluid vial, a syringe into which the fluid is to be drawn up, and a sleeve, in which the sleeve is configured to cover the needle before, during, and/or after the fluid is drawn up or injected into the vial. The vial top may be made out of rubber, silicone, plastic, or any other material which can keep fluid contained. Only the needle, and not the sleeve, would penetrate the top of the vial so as to protect the needle from contamination while the fluid is drawn up or injected, depending on the intended use. The method may additionally include introducing the distal section of the needle into the material at the top of the vial; advancing the distal section of the injection needle into the vial far enough to contact the fluid and to allow it to be drawn up or injected, depending on whether the fluid was being drawn up or injected into the vial/device. This may include inserting the needle until it touches the bottom of the vial. Such needles, if the material being drawn up is a fluid, or fluid based medication, may contain a filter, such as a 5 micron filter. A fluid can include a liquid, a gas, a gel, a medication, or any combination thereof.

Herein, systems or devices which include a sheath or sleeve to cover a needle before and during injection can be referred to as a guarded injection device (GID).

FIG. 1 illustrates an exemplary injection system 100, according to some embodiments of the current subject matter. FIG. 1 illustrates the system 100 prior to performing an injection or drawing up fluid, wherein the fluid can be medication, gas, tissue, or any combination thereof. The following discussion illustrates use of the system 100 in connection with performing intraocular injections. However, the system 100 can be used for performing any type of injection; for drawing up fluids, including medication and gas; or for taking tissue or fluid samples for further evaluation. The system 100 can be configured to prevent and/or substantially reduce incidence of infections (such as intraocular infections) during and/or after performing an injection.

As shown in FIG. 1, the system 100 includes a syringe body 106 that encloses a fluid reservoir 105 for containing an injection fluid 108. The system 100 further includes a plunger 112 having a handle 114 that is disposed outside the syringe body 106 at its proximal end. The syringe body 106 can be configured to be coupled to a needle 104. The needle 104 can be hermetically coupled to the syringe body 106 at its distal end to ensure that the injection fluid does not leak out and is maintained in a substantially sterile condition prior to injection. During injection, the plunger 112 can be coupled to push the platform 110 that can be configured, upon application of an external force to the handle 114 (such as, medical professional pushing the handle 114 toward the syringe body 106), to cause the fluid 108 to egress from the fluid reservoir 105 via the needle 104 and into an injection site (e.g., an eye of a patient in cases of intraocular injections).

The system 100 further includes a sleeve or a sheath 102 that can be configured to be coupled to the syringe body 106 at its distal end, as shown in FIG. 1. The sleeve 102 can be configured to extend along the length of the needle 104. In some embodiments, the sleeve can be further configured to be longer than the needle 104. Alternatively, in some embodiments, the sleeve can be shorter than or the same length as the needle 104. The sleeve 102 can be manufactured from a collapsible material, such as plastic, silicone, medical grade silicone, Polyethelene (PE), TetraFluorEthylene-Perfluorpropylene (FEP), PerFluoroAlkoxy (PFA), any other suitable or similar material, or any combination thereof. The sleeve 102 can be configured to protect the needle 104 from exposure to external contaminants (e.g., air molecules, viruses, sputum, dirt, dust, etc.). It is further configured to keep the needle sterile before and during the injection, thereby ensuring prevention and/or substantial reduction of incidences of infection. In some embodiments, the sleeve can be closed at its distal end, so as to keep the needle sterile prior to use. The needle can be configured to penetrate the sleeve prior to entering the tissue.

The sleeve material can be a non-rigid, non-resilient material that easily collapses, but that may not return back to an initial position or configuration. The sleeve material can be processed or patterned to facilitate collapse, such as by etching, scoring, or folding the material to provide areas along which the sleeve will fold or collapse more readily. Patterning can be accomplished by mechanical deformation, laser ablation, chemical etching, and the like.

The sleeve material can resist only slightly before collapsing, such that the force needed to apply an injection with a sleeve is increased by only a small amount as compared to when using a bare needle. A small increase in the force needed to apply an injection can include an increase of 50% or less, such as 40% or less, 30% or less, 25% or less, 20% or less, 15% or less, and 10% or less. A small increase in the force needed to apply an injection can include an increase of 25% or less. Such sleeve material can make up a sleeve that is permanently attached to an injection system, for example at a needle hub, and can be meant to be used once and disposed of with the needle.

In some embodiments, the sleeve 102 can be configured to be permanently coupled (e.g., via glue, medical grade glue, flow-able silicone adhesive, welding, stapling, sewing, and the like) to the distal end of the syringe body 106. In alternate embodiments, the sleeve 102 can be configured to be detachably coupled (e.g., using snap-on, threads, locks, male/female connection, friction, shrink wrap, and the like) to the distal end of the syringe body 106. The sleeve can also be configured to be attached to the hub of the needle. The attachment can be done through the use of friction, glue or other means. The sleeve size in some embodiments will vary depending on the hub size as it is an attachment point, and in some embodiments the sleeve can be tapered. The tip can be narrower near the end of the needle, and the base wider near the hub. In some embodiments the needle is detachable from the syringe.

Figure 2:
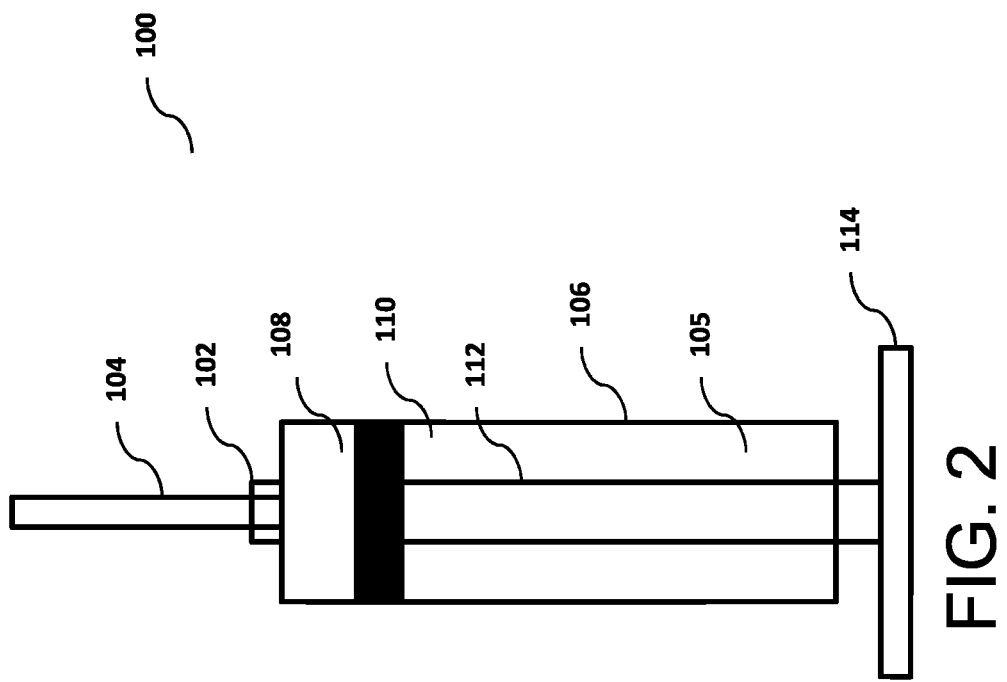
FIG. 2 illustrates the device shown in FIG. 1 after the injection is performed.

During an injection, the needle 104 is configured to be brought into proximity of a surface at a desired injection site. Using the syringe body, a medical professional performing an injection can apply pressure to the injection site to penetrate its surface, thereby piercing it. Upon piercing the surface of the injection site, the needle 104 can be configured to enter the injection site. During the injection, the sleeve 102 is not inserted into the injection site and continues to cover a portion of the needle 104 that is not submerged under the surface of the injection site, thereby maintaining sterility of the exposed portion of the needle. As the needle is pushed deeper underneath the surface of the injection site, the sleeve 102 can be configured to shrink or collapse, as shown in FIG. 2. An amount of length of the sleeve 102 that is configured to remain un-shrunk or un-collapsed can be configured to depend on the amount of the needle 104 configured to remain above the surface of the injection site. Shrinkage or collapse of the sleeve 102 increases as the needle 104 is pushed deeper underneath the surface of the injection site. In some embodiments, the sleeve 102 can be configured to remain coupled to the distal end of the syringe body 106 before, during, and after the injection into the injection site. In alternate embodiments, the sleeve 102 can be configured to disengage from the syringe body 106 upon completion of the injection and/or removal of the needle from the injection site. The sleeve can be used with other protective measures or components, such as retractable needles.

In some embodiments, the material from which the sleeve 102 is manufactured can depend on a type of injection, a type of fluid being injected, a type of the injection site, condition of the injection site, tenderness of the tissue, etc. For example, for intraocular injections, the material that the sleeve 102 can be made of includes a soft material in order to prevent damage to the patient's eye, insertion of the sleeve 102 into the surface surrounding the injection site, or to prevent both insertion of the sleeve 102 into the surface surrounding the injection site and damage to the patient's eye.

In some embodiments, the material for the sleeve and/or syringe needle can also be pretreated with an antimicrobial agent. In some embodiments, the sleeve and/or the needle can be pretreated, coated, impregnated, or protected with any medication, agent, solution, etc. Such pretreatment, coating, impregnation, or protection can be based on the use, type of injection, type of fluid being injected, the injection site, condition of the injection site, and tenderness of the tissue. Such pretreatment, coating, impregnation, or protection can further reduce risk of contamination and/or incidence of infection. Potential coating agents include antibiotics, antifungal, antiviral, anesthetics, lubricants, adhesives, antimetabolites, or such other medications or class of medications as are appropriate for the designated procedure. A medication can include an antibiotic, an antiviral medication, an anti-inflammatory drug, or any combination thereof. An agent can include colloidal silver or any other suitable form of silver, colloidal gold, photocatalytic particles, antimicrobial chemicals, or any other substance that kills or inhibits the growth of microorganisms including bacteria, fungi, or protozoans.

Figure 3A:
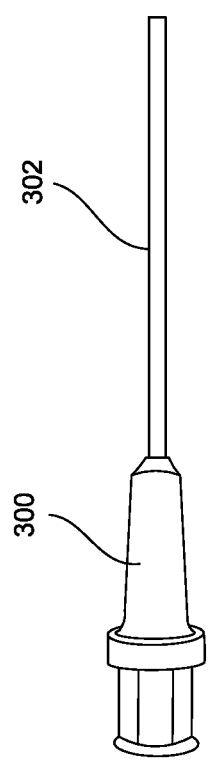
FIG. 3A illustrates an implementation of a device prior to drawing up a fluid from a vial.
Figure 3B:
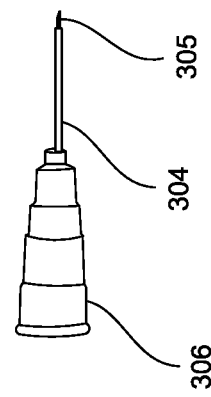
FIG. 3B illustrates an implementation of a device prior to intravitreal injection in which the sleeve is slightly shorter than the needle.

FIG. 3 illustrates an exemplary injection device 300, according to some embodiments of the current subject matter. The device 300 can be any injection device and can include a sleeve 302 that can be placed over a needle. The sleeve 302 can be used to protect the needle (covered by the sleeve 302) before and during the time when a medicine (or any other fluid) is drawn up from a medicinal vial (not shown in FIG. 3) by a medical professional so as to reduce the risk of microbial contamination of the medication. The sleeve 302 can be similar to the sleeve described above with regard to FIGS. 1-2. Once the medicine is drawn up from the medicinal vial, the needle which the sleeve 302 covered is removed and is exchanged with a component 306 that can be configured to be coupled (i.e. glued, snapped, secured, or otherwise can form part of) the injection device 300. The component 306, can include an injection needle 305 that can be covered by a sleeve 304. The injection needle 305 can be used for injection purposes. The sleeve 304 can protect the needle 305 by covering it at least partially before and during the injection.

Use of different needles for drawing up fluid from a vial (or any other container) and for injection can prevent contamination of the needles as well as subsequent infection of the injection sites. In some embodiments, the needle gauge/size can differ between the needle used for drawing fluid and for injection. For example, the device 300 can be used with a 19G (gauge) needle (over which the sleeve 302 is placed) for the purposes of drawing up the fluid from the medicinal vial and a 33G needle (305 shown in FIG. 3) for the purposes of injection. The 19G needle can have a filter so as to reduce the risk of contamination of the fluids or drugs in solution. The needle can be longer, or it can be shorter depending on the use. For example, for drawing up medications, a short 19G needle can be configured so that when it is inserted into specific fluid vials, it will insert just far enough with the tubing collapsed so that the needle tip just enters the vial and is able to draw out a majority of the fluid/medication when the vial or container is inverted upside down without further insertion/withdrawal of the tip of the needle.

As can be understood, any suitable gauge(s) or lengths can be used. For drawing up fluid from a vial, tissue, organ, or cavity suitable gauges for a needle can include 14, 15, 16, 17, 18, 19, 20, 21, 22, 23, 24, 25, 26, 27, 28, 29, 30, 31, 32, 33, or 34, and suitable lengths can varying from 2 mm to 12 inches. For drawing up medications or fluid from a vial, suitable needle sized can more preferably include 16, 17, 18, 19, 20 and 21 gauge needles with a length of ½ inch to 2 inches. For injections, 16, 17, 18, 19, 20, 21, 22, 23, 24, 25, 26, 27, 28, 29, 30, 31, 32, 33, or 34 G needles can be suitable gauges, and these gauges can be used with a needle of 0.157 inches (4 mm) to 12 inches in length, depending on the application. Suitable dimensions for needles to be used for intravitreal injections into the eye include 20, 21, 22, 23, 24, 25, 26, 27, 28, 29, 30, 31, 32, 33, and 34 gauge for the diameter with a length of 0.118 inches (3 mm) to ½ inches. It can be understood that fractional gauges such as 20.5 gauge, or fractions between the sizes listed above, could also be used should they be available. In some embodiments, various injection forces can be used with the component 306.

In some embodiments, use of the component 306 can require the medical professional performing an injection to apply extra injection force before, during, or both before and during the injection in order to collapse the sleeve. Such extra injection force is preferably less than 25% greater than the normal (or customary) injection force without the sleeve for a particular injection. In some embodiments, the extra injection force can be between 0 and 50% greater than the normal injection force. In some embodiments, the additional or extra injection force needed to collapse the sleeve is less than 100 gram-force. In some embodiments, the additional or extra injection force needed to collapse the sleeve ranges from not greater than 100 gram-force to less than 0.1 gram-force, such as less than 0.01 gram-force, including less than 0.001 gram force. In some embodiments, the additional or extra injection force needed to collapse the sleeve ranges from not greater than 100 gram-force to less than 0.00001 gram-force. In some embodiments, the additional or extra injection force needed to collapse the sleeve can approach 0 gram-force.

The force needed to collapse the sleeve as measured when advancing a needle with a protective sleeve into a simulated human sclera (developed by InvenGen (InvenGen, Reading, Pa.)) at a rate of 100 microns per second can range from 0.00001 gram-force to 100 gram-force, such as from 0.0001 gram-force to 100 gram-force, 0.001 gram-force to 100 gram-force, 0.01 gram-force to 100 gram-force, and including 0.1 gram-force to 100 gram-force. In some embodiments, the force needed to collapse the sleeve as measured when advancing a needle with a protective sleeve into a simulated human sclera (developed by InvenGen (InvenGen, Reading, Pa.)) at a rate of 100 microns per second can range from 0.1 gram-force to 100 gram-force. The force needed to collapse the sleeve as measured when advancing a needle with a protective sleeve into a simulated human sclera (developed by InvenGen (InvenGen, Reading, Pa.)) at a rate of 100 microns per second can range from 0.00001 gram-force to 90 gram-force, such as from 0.001 gram-force to 90 gram-force, 0.01 gram-force to 80 gram-force, and including 0.1 gram-force to 75 gram-force. In some embodiments, the force needed to collapse the sleeve as measured above can range from 0.0001 to 70 gram-force, including from 0.0001 to 60 gram-force, from 0.0001 to 50 gram-force, from 0.0001 to 40 gram-force, from 0.0001 to 30 gram-force, such as from 0.0001 to 25 gram-force. In some embodiments, the force needed to collapse the sleeve as measured when advancing a needle with a protective sleeve into a simulated human sclera (developed by InvenGen (InvenGen, Reading, Pa.)) at a rate of 100 microns per second can range from 0.0001 gram-force to 75 gram-force.

In some embodiments, the force necessary to collapse the sleeve was measured until about 70% of the collapsible portion of the sleeve had compressed or collapsed. In other embodiments, the force necessary to collapse the sleeve was measured until about 60% of the collapsible portion of the sleeve had compressed or collapsed. Depending on the application, such measurements were made until about 50% of the collapsible portion of the sleeve had compressed or collapsed, or 40%, 30%, or 20% of the collapsible portion of the sleeve had compressed or collapsed. The collapsible portion of the sleeve, or the portion of the sleeve capable of collapse, may not include any thickened portion or contamination prevention tip near the distal end of the sleeve that surrounds the needle tip.

In general, when a sleeve is used on a smaller needle, such as a 33G (i.e. 33 gauge) needle for intraocular injection, the upper limit for such extra force is generally no more than 50% greater, and preferably no more than 25% greater than the force using such a needle without the sleeve as measured by advancing the needle with and without the protective sleeve into a simulated human sclera at a rate of 100 microns per second until about 70% of the collapsible portion of the sleeve had compressed or collapsed. In this scenario, either the same needle with and without a protective sleeve can be tested or similar needles, some with and some without protective sleeves, can be tested. Use of an injection force that is more than 50% greater than that normally used for intraocular injection might not result in desirable results, and thus, use of the component 306 might not be in the best interest of a patient. The undesirable results can be the result of increased discomfort and greater risk of injury that occur because of the great amount of force.

When injecting into sensitive areas on a patient, such as the ocular region, it can be desirable to maintain sterility of the needle while inflicting as little additional pain as possible. As mentioned herein above, the protective sleeve can be selected to collapse with little added force. Thus, the sleeve can be made of a material that is not rigid, nor resilient, and that will easily collapse under pressure. Such a material may not spring back to an initial position after the pressure or added force dissipates or is removed. Protective sleeves made of such material may not be ideal for protective use both before and after injection. Protective sleeves made of such non-rigid, non-resilient material may be suitable for protective use before and during an injection or needle insertion, such that the protective sleeve covers the needle at least partially during those periods.

TABLE 1 illustrates the range of forces associated with various materials and configurations of needles with protective sleeves. Both 19 and 33 gauge needles were tested by recording the amount of force needed for the needles to enter a material similar in consistency to the human sclera. The material used to simulate the human sclera was developed by InvenGen (InvenGen, Reading, Pa.) and was selected because of its high signal-to-noise properties that cause it to be used by ophthalmic device manufactures. Cross head speeds, which determined the rate of insertion of the needles into the material, for the test set, were kept constant at 100 microns per second. This rate provided good needle tip and cutting edge force resolution. A force profile was generated for the needle tip entry to highlight the effect of tip geometries. Test sets that gauged repeatability and reproducibility data for similar products showed good test set capability for accurate measurements, with total gauge errors in the 5 to 15% range. The needles were advanced into the test media at the rate of 100 microns per second until about 70% of the collapsible portion of the sleeve had compressed or collapsed.

The tests described below show that the amount of force needed when employing medical grade thick silicone was not optimal in terms of increasing the requisite force applied by 50% or less when compared to a bare needle. The amount of force required for injections that used a thick silicone sleeve over the 33G needle was 131.1 gf (gram-force). This value was over 50% greater than the force required without the sleeve, 58.9 gf, for a 33G needle. For the injections that used a thick silicone sleeve over the 19 G needle, the average force was 692.7 gf as compared to 224 gf for a bare 19G needle (TABLE 1). This value of 692.7 gf surpassed the 50% or less additional force criteria. Thus, the thick, resilient silicone sleeve over the 19 G filter needle (the sleeve having dimensions of 0.125 inches outer diameter, 0.064 inches inner diameter; and approximately 0.061 inch thickness) is not ideal for the intended use. Thick, resilient sleeve or sheath materials can be characterized by the tendency to return to an initial configuration after an injection, such that if a resilient sleeve initially covers the entire length of a needle, the sleeve will cover the entire needle again after an injection. Such sleeves that include thick, resilient material typically can require force above the desired 100 gf additional force threshold to successfully collapse the sleeve and administer an injection. Such sleeves can also exceed the 50% increase in force needed to make an injection threshold as well. As such, these types of thick, resilient sleeves generally can be unsuitable for use in applications where minimum force is needed.

Conversely, the material used for the 33G needle with a dumbbell-configured sleeve worked well. With the combined sleeve data for the longer (2.5 mm×1) and shorter (1.5 mm×5) end additions of an early production runs of the dumbbell design, the average force required was 81.6 gf with the sleeve and 58.96 gf without the sleeve (Table 1). The difference was a 22.64 gram-force difference, which is right on the margin of detection, and corresponds to 38.4% more force. The internal diameter (ID) of the long narrow portion of the sleeve 602 was 0.01 inches and the outer diameter (ID) of the sleeve was 0.015 inches, for a wall thickness of 0.0025 inches, which worked well for the smaller needles. The outer diameter (OD) of the needle was 0.008 inches and the distance between the needle and the internal diameter (ID) of the silicone sleeve totaled 0.015 inches (i.e. on both sides, or 0.00375 inches on each side).

While it is possible to reduce the distance between the ID of the silicone sleeve and the OD of the metal of the needle by a small, finite amount, if it is reduced to be much less than 0.00375 inches on each side, the resistance increases, and the amount of force for insertion also increases. With such small differences between the needle's outer diameter and the sleeve's inner diameter, there is also a tendency for the sleeve to roll in on itself, as opposed to collapsing, unless a second piece is secured to the tip to prevent this from happening, as in the dumbbell shaped version. Smaller distances between the sleeve and needle also become problematic because the production tolerances of the sleeve materials ID and the needle OD can vary and can lead to contact, friction, and the need for more force for injection, particularly with the smaller needles and sleeve sizes.

In general, sleeve material tolerances tend to vary more than needle tolerances. In other words, the ratio of the space between the sleeve and the needle to the size of the needle can vary with the material used for the protective sleeve. For materials with larger variances, the ratio of the (Sleeve ID-Needle OD)/(Needle OD) will need to be higher. Tubing materials with smaller production tolerances and variance in ID are preferable for this reason. The ratio between the difference between the inner diameter of the sleeve and the outer diameter of the needle divided by the outer diameter of the needle, (Sleeve ID-Needle OD)/(Needle OD), can be between 1/20 and 6. Additionally, the ratio between the difference between the inner diameter of the sleeve and the outer diameter of the needle divided by the outer diameter of the needle can be between 3 and 5 for sleeves of wall thickness of 0.0005 inch on a 19G needle. Alternatively, the ratio between the difference between the inner diameter of the sleeve and the outer diameter of the needle divided by the outer diameter of the needle can be between 0.1 and 0.3 for sleeves with a wall thickness of 0.0025 inches on a 33G needle.

In some embodiments, it is desirable to use existing packaging material for transporting a needle. In some such embodiments, the outer diameter of a sleeve protecting a needle can be of a suitable thickness and/or outer diameter so as to allow for easy insertion and removal of a needle with a protective sleeve from the existing packaging material. The existing packaging material can include a hard plastic casing that keeps the needle sterile and prevents needle sticks prior to use.

Figure 6:
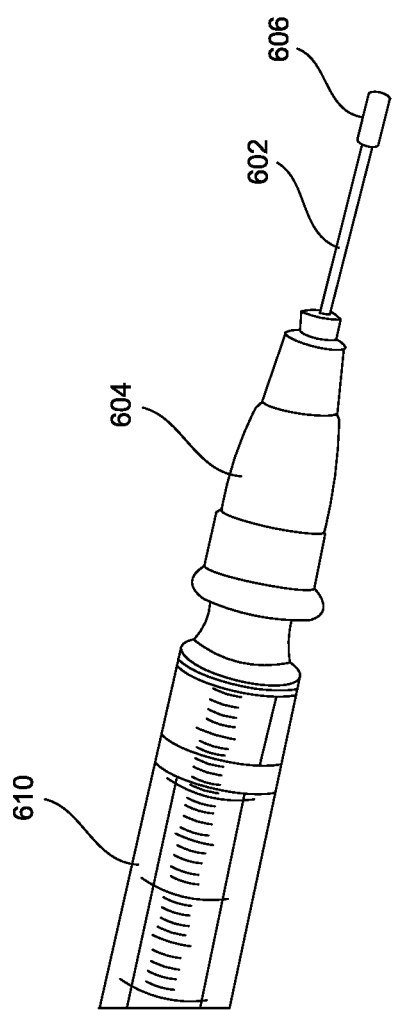
FIG. 6 illustrates an exemplary injection device attached to a syringe prior to an injection, according to some embodiments of the current subject matter.

For the dumbbell shaped version represented in FIG. 6, the thinner tubing used for the main portion of the sleeve has a second piece of tubing added to the tip measuring about 1.5 to 2.5 mm long with an internal diameter of 0.020 inches and an outer diameter of 0.037 inches, and a thickness of 0.017 inches. The additional tubing at the tip of dumbbell shaped version helps to reduce the risk of the rest of the sleeve entering the injection site, or of rolling in on itself and contaminating the needle. This combination works well, and the parameters of this version work well when the intended use is intraocular injections, and intravitreal injections in particular.

For intraocular injections when no lid speculum is required, it can be, in some embodiments, beneficial to have a sleeve with either some resistance to moving or that is not significantly affected by movement of the lids, such a silicone tubing or similar material with a thickness between 0.010 inches and 0.001 inches, particularly those between 0.0075 inches and 0.0025 inches. On the other hand, in the event a lid speculum is used, the thinner material between 0.001 inches and 0.0001 inches, or even less as manufacturing techniques of these thin materials improve, may be used. For example, the use of 0.0005 inches wall thickness PE, PFA, or FEP can be more reasonable, although some health care workers may prefer one over the other for different reasons. Use of a small piece of tubing at the tip of a 0.0005 inch sleeve to insure the sleeve does not enter the injection site, and does not contaminate the needle, provides additional stability and safety, such that the thinner walled 0.0005 inches sleeve material can be used in devices for intravitreal injection without a lid speculum. In some embodiments, the thinner walled materials, such as the 0.0005 inch material, can be used without a speculum as well by those who prefer the benefits of the lower forces that are typically required to collapse thinner walled tubing or sleeves.

For a 19G filter needle, the difference between the inner diameter (ID) of the PE, PFA, or FEP sleeve and the outer diameter (OD) of the needle can be about 3 to 5 times that of the outer diameter of the needle. This ratio can vary as indicated around the 0.05 to 6 times range depending on the application. The size of the needle hub also impacts the size of the sleeve, as it easier to secure an appropriately sized sleeve to the hub by friction, eliminating the need for additional adhesives to secure a sleeve on hub. A range of 3 to 5 times works well with existing hub sizes on the 18 and 19 gauge Becton Dickison™ needles. In the event the hub size is changed or varies for different manufacturers, the preferred range would likely change to closer match these hub sizes.

The dimensions of the protective sleeve can also be influenced by the size of the plastic casing surrounding the needle during shipping. The sleeve diameter can be less than the internal diameter of the casing so as to allow easy insertion into and removal of the plastic casing before and after shipping of the needle with a protective sleeve.

When the eyelids are held, blinking is less likely, and the 0.0005 inch wall-thickness material becomes more feasible. In some cases, a cone-shaped taper at the tip may be desirable. For drawing up fluids/medications/gas from a vial, or to protect a needle prior to insertion into an IV tube or the like, where the risk of the sleeve being brushed aside is low, the use of thinner materials in the 0.001 inch to 0.0005 inch wall thickness can be preferred. Even thinner materials can be used as they become available, as these thinner materials can require less force to displace. Use of less force to displace a protective sleeve can be safer and can help reduce user fatigue. A needle protected by a thin sleeve can also be easier to use in combination with other needle safety devices. The sleeve thickness can depend on the use and the desired amount of resistance for a particular application.

It can also be possible to sculpt the silicone, PE, PFA, or FEP tubing with a laser to create ribs and/or partial thickness slices to help insure the sleeve collapses with less force and/or in a more controlled fashion.

TABLE 1

Injection Force Data

| Envelope | Sample Number | Description | Max Force, grams (f) | Notes |
|---|---|---|---|---|
| 2 | 1 | 33 Ga. Thick Sleeve | 131.1 | Needle penetrated media by at least 4 mm |
| 10 | 1 | Draw Up Needle - BD 19 Gauge Filtered Needle, Very thick silicone tube | 604.0 | Test stopped. Needle though media at 604 grams (f). Max'ed out 8.8 N. force gauge |
| 10 | 2 | Draw Up Needle - BD 19 Gauge Filtered Needle, Very thick silicone tube | 781.4 | Max reached before gauge capacity exceeded. |
| 10 | 1 | BD 19 Ga. Filtered Needle without silicone tubing | 224.0 | 170 grams (f) at full needle OD. |
| 11 | 1 | BD 19 Ga. Filtered Needle × 1.5 inches lg. with silicone tubing | 767.1 | Max reached before gauge capacity exceeded. |
| 11 | 2 | BD 19 Ga. Filtered Needle × 1.5 inches lg. with silicone tubing | 685.7 | Max reached before gauge capacity exceeded. |
| 12 | 1 | 33 Ga. Needle with 0.0005 inches Sleeve | 79.3 | |
| 12 | 2 | 33 Ga. Needle with 0.0005 inches Sleeve | 58.8 | |
| 1 | 1 | 33 Ga. Needle with thinner Dumbbell Sleeve - Shorter | 79.2 | |
| 1 | 2 | 33 Ga. Needle with Dumbbell Sleeve - Shorter | 87.7 | |
| 1 | 3 | 33 Ga. Needle with Dumbbell Sleeve - Shorter | 81.3 | |
| 1 | 4 | 33 Ga. Needle with Dumbbell Sleeve - Longer | 76.1 | |
| 1 | 5 | 33 Ga. Needle with Dumbbell Sleeve - Shorter | 85.1 | |
| 1 | 6 | 33 Ga. Needle with Dumbbell Sleeve - Shorter | 80.2 | |
| 1 | 7 | 33 Ga. Needle, no sleeve | 62.0 | |
| 1 | 8 | 33 Ga. Needle, no sleeve | 58.4 | |
| 1 | 9 | 33 Ga. Needle, no sleeve | 61.4 | |
| 1 | 10 | 33 Ga. Needle, no sleeve | 59.5 | |
| 1 | 11 | 33 Ga. Needle, no sleeve | 53.5 | |

Figure 4:
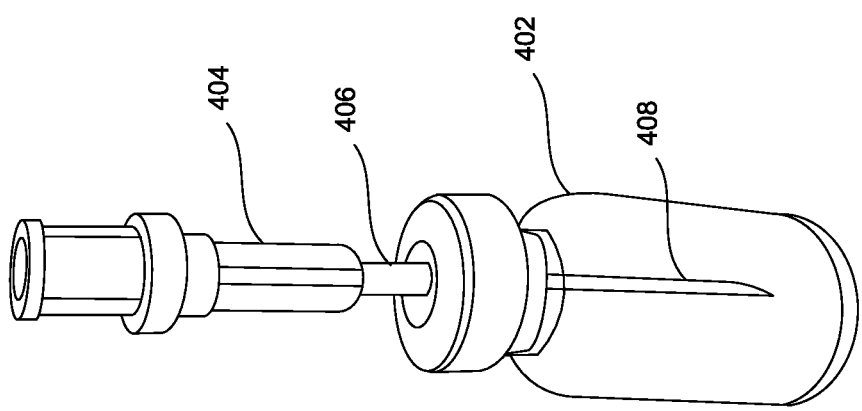
FIG. 4 illustrates an implementation of a needle device subsequent to insertion into a vial.

FIG. 4 illustrates a needle device subsequent to insertion into a medicinal vial 402, with the sleeve 406 collapsed on top of the vial stopper, and the needle without the sleeve 408 extending to the bottom of the vial 402 so as to allow fluid (e.g. medication, liquid, gas, gel) or other material to be drawn up into the injection device 404 while reducing the risk of contamination according to some embodiments of the current subject matter. The medicinal vial 402 can be configured to contain any type of medicine that is capable of being transferred into the injection device 404. The injection device 404 can be configured to have a body that is coupled to a needle 408 (shown inside the vial 404) and a sleeve 406 (shown in a collapsed state). The sleeve 406 can be similar to the sleeves shown in FIGS. 1-3. Alternatively, it can be thinner and can be positioned to collapse around the hub of the needle at 404 rather than around the needle.

Figure 5:
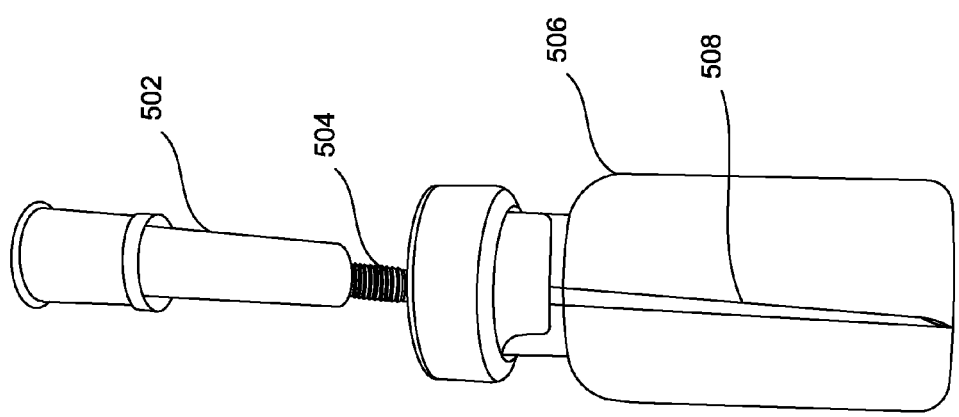
FIG. 5 illustrates an exemplary needle device with the sleeve collapsed on top of the vial stopper subsequent to insertion into a medicinal vial, according to some embodiments of the current subject matter.

FIG. 5 illustrates another exemplary needle device 502 with the sleeve 504 collapsed on top of the vial stopper subsequent to insertion of the needle 508 into a medicinal vial 506. The medicinal vial 506 can be configured to contain medicine for transferring into the injection device 502. Similarly to the injection device shown in FIG. 4, the injection device 502 can be configured to have a body that is coupled to a needle 508 (shown inside the vial 506) and a sleeve 504 (shown in a collapsed state). The sleeve 504 can be similar to the sleeves shown in FIGS. 1-4.

Figure 7:
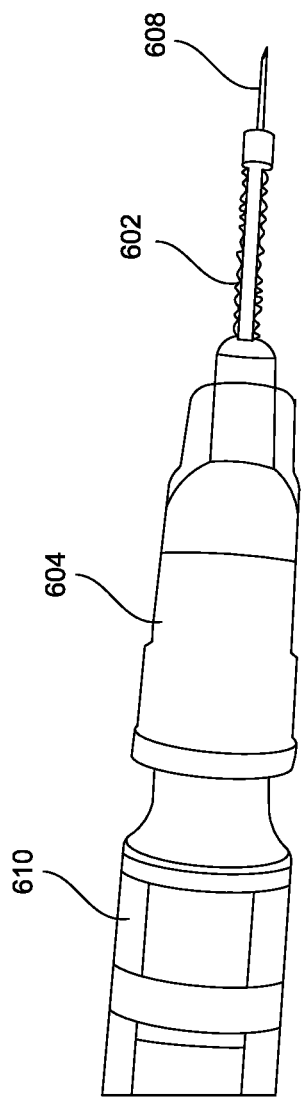
FIG. 7 illustrates an exemplary injection device subsequent to an injection, according to some embodiments of the current subject matter.

FIGS. 6 and 7 illustrate an exemplary injection device 610 that includes an injection device body coupled to an injector needle component 604 (having a hub similar to the component 306 shown in FIG. 3) and a needle 608 that is covered by a sleeve 602. FIG. 6 illustrates the injection device 610 prior to injection and FIG. 7 illustrates the injection device subsequent to injection. As shown in FIG. 6, prior to injection, the sleeve 602 can be configured to fully cover the needle 608, thereby protecting it from contamination or otherwise exposure to contaminants (such as airborne saliva, and the like). During injection, the sleeve 602 is pulled back toward the body of the injection device 610, thereby collapsing the sleeve 602 and exposing the needle 608. After the injection (as shown in FIG. 7), the sleeve 602 may remain pulled back, and needle 608 can be exposed since after the injection the needle 608 is typically disposed of, and there is not further risk of contamination affecting the patient. Additional devices, such as those to prevent needle sticks to medical personnel can be attached to the device, to reduce the risk to health care workers as well.

In some embodiments, the injection device illustrated in FIGS. 1-7 can be effectively used to reduce the risk of infection when fluids/medications/gas are drawn up from a vial or fluid/tissue is removed for therapeutic or diagnostic purposes. In some embodiments (as shown, for example, in FIGS. 6-7), the injection device includes an additional tubing 606 that is larger than the sleeve and can be affixed on to the tip to stabilize the tip and to prevent contamination from saliva or contaminants sliding down the sleeve from gravity, This tip can give the needle-hub combination (604, 602, 606) the shape of a dumbbell. A needle with a dumbbell would be the same as a needle with a contamination prevention tip (CPT) on a surrounding, protective sleeve. The CPT can also results in a more controlled injection. Another potential benefit of the additional tubing (i.e. contamination prevention tip) 606 is the reduction of likelihood that the thinner portion of the sleeve, 602, will enter the injection site. Preventing the protective sleeve from entering delicate areas, such as the area beneath the conjunctiva or sclera of the eye, can be important, and the additional tubing 606 can make the configuration shown in FIGS. 6 and 7 more desirable for use near these tissues than the configuration shown in FIG. 3A. This configuration can have the added benefit of preventing contaminants from sliding down the sleeve 602 and reaching the needle tip.

For example, a 33-gauge, TSK Laboratory brand, sterile, disposable needle can be fitted with tubing of exemplary dimensions of 0.010 inches ID and 0.016 inches OD. Such a 33 Gauge needle can have an added component 606 (shown in FIGS. 6-7) of 0.020 inches ID×0.037 inches OD that is coupled with silicone adhesive, glued, snapped, and/or otherwise secured on the tip of the sleeve 602. The added component 606 can be configured to cover the end of the overall sleeve and can range from 1.0 to 7 mm, such as from 1.5 to 2.75 mm, for use with a ½ inch needle, and in such cases, the component 606 can most preferably be 2.5 mm. As can be understood, other sizes are possible. In some embodiments, the component 606 can be manufactured from silicone, plastic, glass, and/or any other suitable material, and/or any combination thereof. The component 606 can be flexible, semi-rigid, semi-flexible, rigid, and/or any combination thereof.

It can be desirable to insert a needle a known distance beneath the surface of a tissue or structure. A guide can be used to indicate to a user when the needle has penetrated a predetermined distance. The guide can be an indicator or a depth-limiting component. An indicator can include etched, painted, or anodized markings on the inserted needle. In some embodiments, an injection system that includes a needle or other injection device and a protective sleeve can also include a depth-limiting component. A depth limiting component can include a rigid outer tube extending from the needle hub distally (towards the needle tip) a fixed distance, a rigid tube extending from the larger tip portion of a protective sleeve back towards the needle hub, or a similar device. A depth-limiting component can limit the depth of the injection into a tissue, for example the eye, a finite and predetermined amount. For example, for intravitreal injections, the tube could be sized to allow the needle to enter the eye 3 to 4 mm. The inner diameter of the outer rigid tube could be large enough to have sufficient clearance with the outer diameter of the inner protective sleeve, so as not to increase the amount of force needed collapse the inner protective sleeve during injection.

Figure 8:
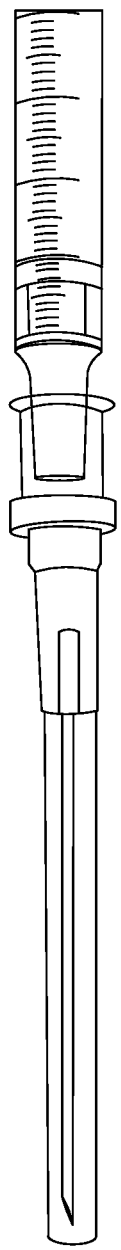
FIG. 8 illustrates a 19G filter needle with a 0.0005 inch wall thickness clear plastic sleeve, attached to a syringe.

FIG. 8 illustrates a 19G filter needle with a 0.0005 inch wall thickness clear plastic sleeve, attached to a syringe. The sleeve material can include TetraFluorEthylene-Perfluoropropylene (FEP), PerFluoroAlkoxy (PFA), Polyethelene (PE) or similar materials, including any combination thereof. These materials can additionally be coated with Polybutylene. Polybutylene in combination with the other polymers listed can make a material that is ideal for use in needles used to draw medications out of vials with spongy rubber stoppers that are typically made of polyisoprene or similar materials, or for use on other needles like butterflies, blood draw needles, and intravenous (IV) catheters, where there is less risk of moving parts like the lid dislodging the material during insertion. The 0.0005 inch wall thickness sleeve material, or similar very thin materials, are also preferable for applications where it is desirable to have minimal additional force created by the sleeve during insertion of the needle. Additionally, a small piece of silicone tubing can be placed at the tip of the 19 G needle. The small piece of silicone tubing can have any suitable dimensions, including 0.15 inches (4 mm) in length, 0.065 inches (1.651 mm) in inner diameter, and 0.075 inches (1.5 mm) in outer diameter. To the outer wall of this, the 0.0005 inch thickness sleeve material can be attached by friction, glue, or other adhesive to prevent the thin material from rolling on itself and contaminating the needle, or from entering the injection site with the needle.

Figure 9:
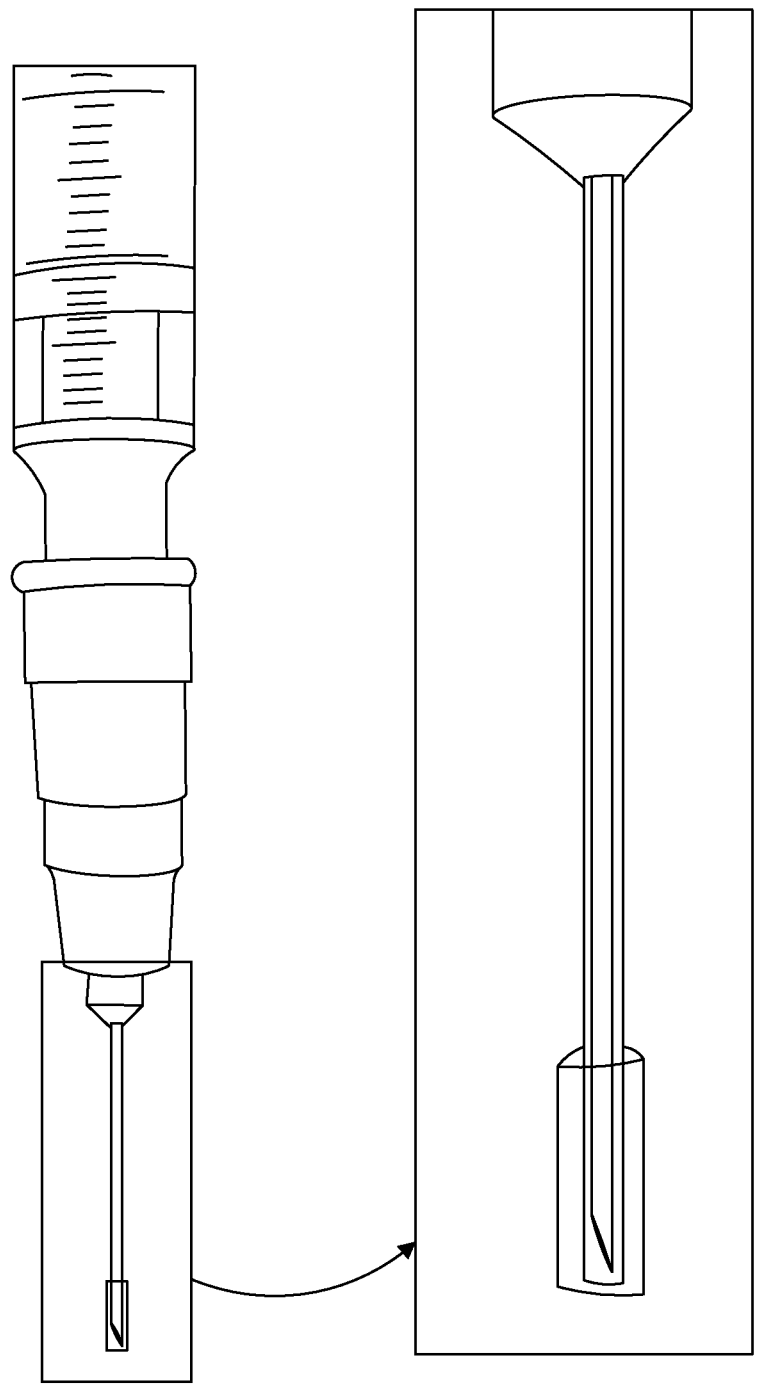
FIG. 9 shows an implementation of a 33G needle with a silicone sleeve with a wider tip.

FIG. 9 is an example of a 33G needle with a silicone sleeve that has a wider tip which helps to accomplish a number of goals, any or all of which can be helpful in any given injection. The wider tip can be achieved by addition of larger diameter tubing on the portion of the sleeve near the needle tip. It can also be fabricated as one piece of material that is wider at one end, by injection molding, or through other methods of producing silicone tubing or similar materials. The added functionality of a wider tip includes preventing contaminants from sliding down the sleeve, helping to stabilize the sleeve during injection, and/or to push the conjunctiva down prior to needle insertion when it is edematous, as can occur from subconjuctiva anaesthetics like lidocaine, or xylocaine. The wider tip also helps to prevent the sleeve tip from rolling in on itself during the insertion process when the sleeve is retracting up the needle. The wider tip also prevents the thinner tubing, covering the rest of the sleeve, from entering the injection site. Without the extra tip thickness/tubing, in some instance the sleeve tip can roll in and bring the outer contaminated sleeve in contact with the needle before it enters tissue, such as the eye. This rolling contaminates the needle and defeats one of the purposes for the protective sleeve.

For this reason, the addition to the tip of a small amount of tubing, for example a 1.5-2.5 mm piece, of a slightly larger silicone sleeve that fits over the protective sleeve, can be helpful in a number of ways. One of the most important functions of the extra material on the sleeve near the needle tip is to ensure the tubing collapses in a way that does not contaminate the needle. This phenomenon is more problematic with the small diameter needles, such as those of 30-34 gauge, with a silicone sleeve, particularly when the sleeve is very snug or tight to the needle. Even small production tolerances and variances of the smaller tubes ID can lead to improper collapse of the sleeve. It is preferable to have some space between the needle and the sleeve to minimize the friction and force needed for the injection, but not so much as to block the view the needle and tissue to be injected. Preferably, on the smaller needles, the ratio=(Sleeve ID−Needle OD)/(Needle OD) is at least 1/20, and not so great that it becomes loose and uncontrolled, as could happen if the ratio was greater than 2. More preferably, for smaller needles, the ratio=(Sleeve ID-Needle OD)/(Needle OD) is between 0.1 and 0.3. For larger needles and sleeves, rolling of the sleeve in on itself was not noted as a problem in experiments as described herein. The thin 0.0005 inch wall thickness sleeves used with the 19G 1½ inch filter needles did not have a sleeve rolling problem. This configuration, however, can have the potential of the protective sleeve entering the injections site, being so thin, and of kinking and contaminating the needle when not sealed or narrow at the end or tip. It can be preferable to place a small piece of tubing on the inside of the sleeve, or alternatively on the outside of the sleeve, to prevent these problems.

However, if the distance between the needle and the sleeve of the very thin 0.0005 inch wall thickness PE, FEP or PFA sleeves becomes too large, the sleeve can become floppy. This floppiness may make it harder to package the needle and sleeve assembly in the hard plastic needle cover that comes with most needles, unless the sleeve is compressed. Packaging a needle and sleeve assembly such that the sleeve is collapsed or compressed is more likely to contaminate the needle and can make a hard cover more difficult to use. In some instances, the ratio=(Sleeve ID-Needle OD)/(Needle OD) can range from about 1/20 to 6. For 19G needles, the ratio=(Sleeve ID-Needle OD)/(Needle OD) can be between 3 and 5. As mentioned earlier, the size of the needle hub 300 or 306 can impact the preferred size of the sleeve, particularly the sleeve ID, as it is preferable to match the sleeve ID to the hub size to reduce or eliminate the need for adhesive to hold the sleeve to the hub 300, 306. In addition, the size of the hard cover used to ship the needle, which is generally plastic, can influence the size of the sleeve, as it is preferable for the sleeve to fit easily inside the cover, making it easier to insert and remove the sleeve into and out of the protective cover without the sleeve becoming damaged or falling off. Doing this can help minimize the need for retooling to manufacture and package needles with the sleeve devices described herein, making them more reasonable, in terms of cost, to produce.

Figure 10:
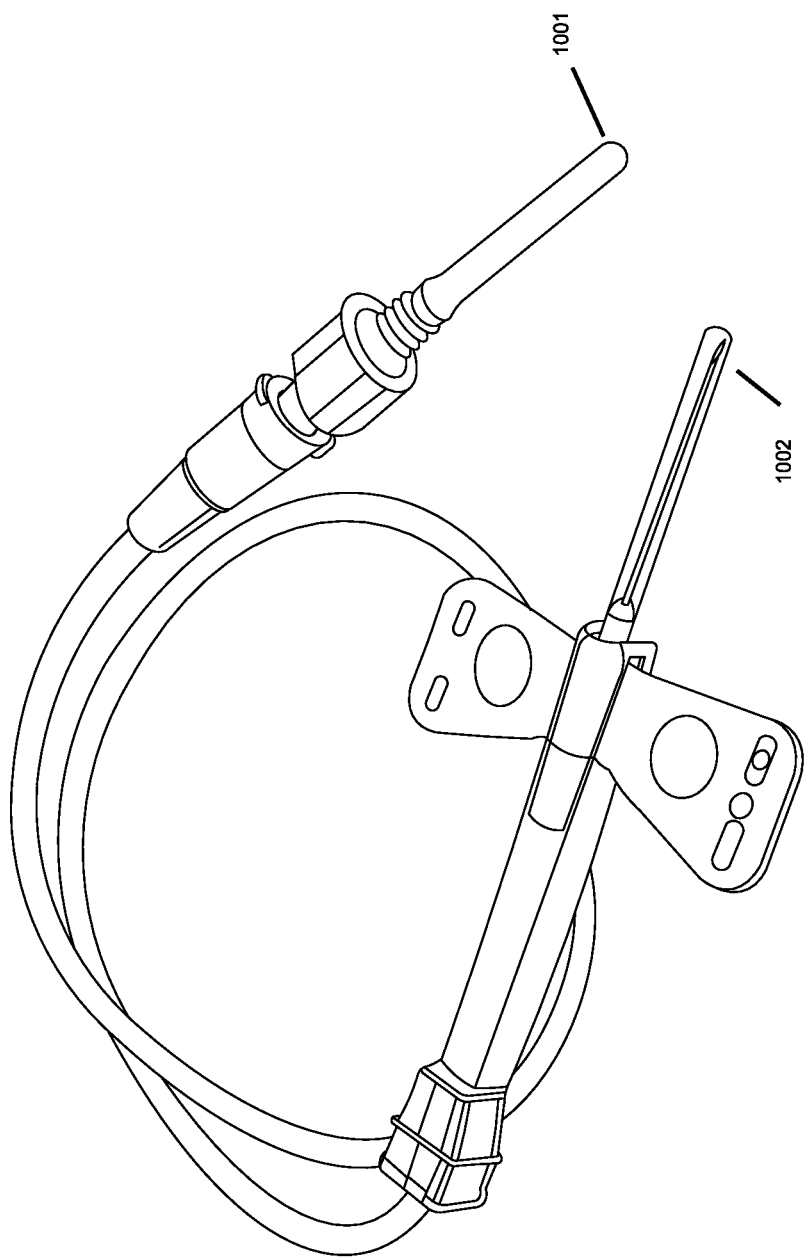
FIG. 10 shows an implementation of a butterfly needle with a clear 0.0005 inch wall thickness sleeve.

FIG. 10 shows an example of a butterfly needle with a clear, 0.0005 inch wall thickness sleeve 1002. The sleeve material can include PE, FEP, PFA, other similar materials, or any combination thereof. The corrugation can ensure that the sleeve collapses in a controlled fashion. FIG. 10 also shows a solid rounded silicone tip 1001 towards the right hand side of the figure. This tip contains a needle inside the covering and is meant to be inserted into a vacutainer. The solid rounded silicone tip 1001 for insertion into a vacutainer is distinct from many of the embodiments described herein. Testing showed that the solid rounded silicone tip 1001 required on average 203.72 gf (gram-force) to collapse the sleeve (see Table 4), which greatly exceeds the target of 100 gf or less to collapse the sleeve. The total amount of force needed for insertion was 540 gf. With 540 gf of force, when the tip finally penetrates the silicone tip 1001, it would require such force that controlling the final location of the needle within the silicone tip would be difficult and potentially pose a hazard for a patient. The silicone tip 1001 also requires 60% more force to insert the needle than the needle alone. The silicone tip 1001 is opaque. This opacity obscures a medical professional's view of the needle, making insertion of the needle beneath the silicone tip difficult and hazardous when working with patients. The thickness of the material used in the silicone tip 1001 and its total covering of the needle would create a risk of contamination when used directly in patients, as the needle may cut a plug of the silicone during penetration, possibly entraining the silicone in the injection, and when the injection was done possibly leaving the silicone behind, thus contaminating the patient or injection site. While in some cases it might be feasible to use such a silicone covering for insertion in patients, such a silicone tip 1001 when used for direct insertion of a needle beneath the tip into a patient would be of a thinner silicone. When drawing up fluid from vials using a filter needle, covering the tip completely is possible. However, the amount of force required to insert such a covered needle into a vial would be different than that required by some embodiments described herein. The device of FIG. 10 is designed for insertion into vacutainers, which is a use generally not suitable for the embodiments described herein.

Figure 11:
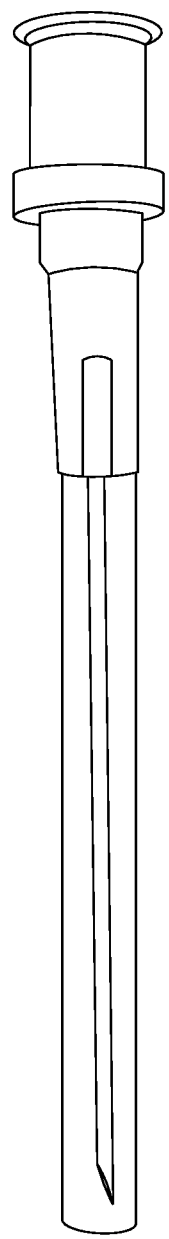
FIG. 11 shows an exemplary 19G filter needle with a thick silicone sleeve.

FIG. 11 shows a 19G filter needle with the thick silicone sleeve whose characteristics are listed in the discussion of TABLE 1. As described herein, such a device with a similarly thick sleeve is unsuitable for many of the applications described, as the force required to collapse the sleeve exceeds the threshold of 100 gf and also exceeds the desired level of less than 50% greater than the force required to perform an injection in the absence of a sleeve.

Figure 12:
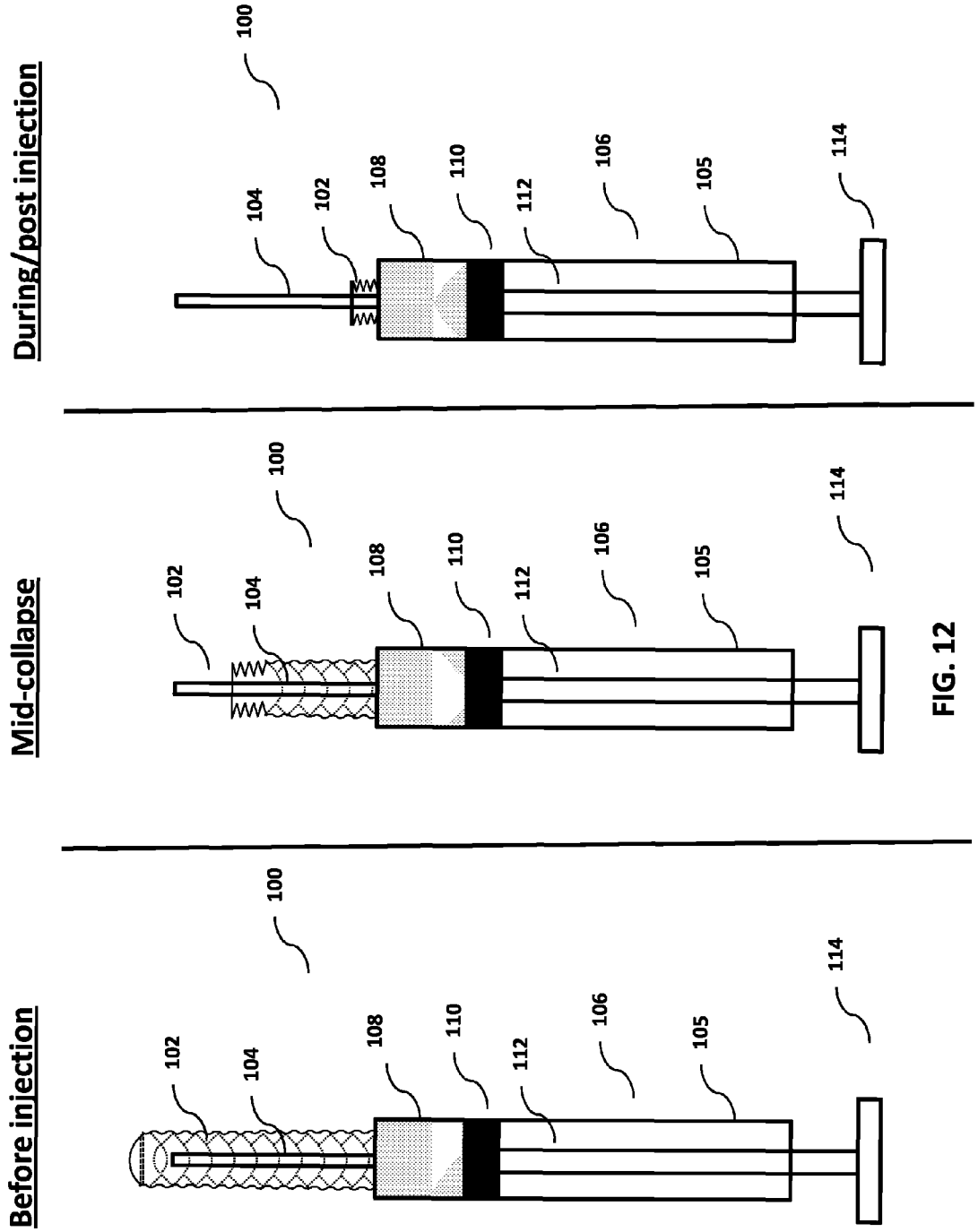
FIG. 12 shows an exemplary injection device of an accordion, or baffle, design to help facilitate a controlled collapse with a sealed or covered tip as might be used with a filter needle so as to prevent the material getting into the syringe.

FIG. 12 illustrates the accordion, or baffle, design that helps to facilitate a controlled collapse with a sealed or covered tip, as might be used with a filter needle so as to prevent the material getting into the syringe. In the far left portion of FIG. 12, the injection device with the sleeve completely covering the needle is shown. The middle portion of the figure illustrates how such a sleeve would appear as it collapses, folding down in a neat, compact manner. The portion of the figure to the far right illustrates the appearance of an accordion, or baffle, design sleeve during injection, and, depending on the sleeve material, post injection as well. As further described herein, the accordion, or baffle, design can be imparted upon the sleeve by etching or folding the sleeve material.

Intraocular injections can be done using the device, for example component 604 in combination with a component 610 shown in FIG. 6. The method of doing this would be first to draw up into component 610 the medication from a vial using a needle such as a 19G filter needle, although others sizes be used. This needle can have a needle guard on it, such as seen in FIG. 8. Prior to injection into the eye, preferably through the pars plana which is located 3-4 mm posterior to the limbus, the 19G needle could be exchanged for a 33G needle with a needle guard, such as seen in FIG. 13B component 602 with widened tip 606. The patient could then be anaesthetized using either topical proparicaine, tetracaine, tetra-visc, or lidocaine 4% or subconjunctival xylocaine or lidocaine 1 or 2% with or without epinephrine. The lids of the patient could then be held open by the doctor or person doing the injection, and the tip 606 could then be placed generally perpendicular to the conjunctiva, although an angled approach is also possible, approximately 3 mm posterior to the limbus in pseudophaks, or 3.5-4.0 mm posterior to the limbus in phakic patients. While holding the outside of the syringe, the tip could be inserted substantially perpendicularly to the eyeball surface, and as the needle 608 enters the vitreous cavity of the eye, the shield/guard 602 and wider tip 606 remain outside the eye.

The protection provided by a protective sleeve can make it safer to not use a lid speculum to hold the eyelids open, as a blink by the patient would contaminate the guard and not the needle. Also, the guard will protect against contamination by the speech of the patient or other people in the room, including the physician, due to contaminated spit particles. While it is generally not necessary to use a lid speculum with this device, one can be used as well. The needle can be inserted until 3 to 4 mm of the needle has entered the injection site, at which point the sleeve can be completely or partially collapsed. In instances where the needle can be inserted only partially, the sleeve may not completely collapse. At this point, the drug can be injected by pressing down on the plunger component 114 (FIG. 12). Once all of the drug has been injected, the needle and protective sleeve can be removed from the eye and discarded. For the needle guards with a contamination prevention tip (CPT), the silicone sleeve can retract back down the needle some distance. In the instances when a needle is used with a CPT, after the needle is inserted into an injection site 3 to 4 mm, the protective sleeve may not return to its original position, and as such the tip end of the needle may not be covered post-injection. In practice, it has been seen that in such instances, after a needle with a CPT is inserted 3 to 4 mm into an injection site, the protective sleeve usually does not return to its pre-injection position. Since the needle is only used once, it is not necessary for the sleeve to retract back over the tip of the needle after an injection.

The injection system can also include components to aid a user in determining the distance between an anatomical feature or other site and the potential injection site, otherwise described as an offset marker. A wider tip can be used for this purpose. Alternatively, an additional premeasured piece of tubing, a ring, a piece of silicone tubing, or other device can be attached to the sleeve near the needle tip as an offset marker. An offset marker can be used to enable the user to know that the distance the needle is inserted from a point, such as the limbus, is a predetermined amount, for example 3 to 4 mm, depending on whether the patient is phakic, aphakic or pseudophakic. The offset marker can be straight, curved, or any other configuration that allows a user to determine the distance from a feature to the needle tip in a reliable manner. The offset marker can be angled forward, backward or at a 90° angle depending on user preference. The offset marker can have marks on it to allow the user to select from multiple options, such as one at 3.0 mm that would be better suited for pseudophakic patients, and 3.5 or 4.0 mm for phakic patients. The distance indicators on the offset marker can be hash marks, variation in color, variation in size, or a combination thereof.

Figure 13A:
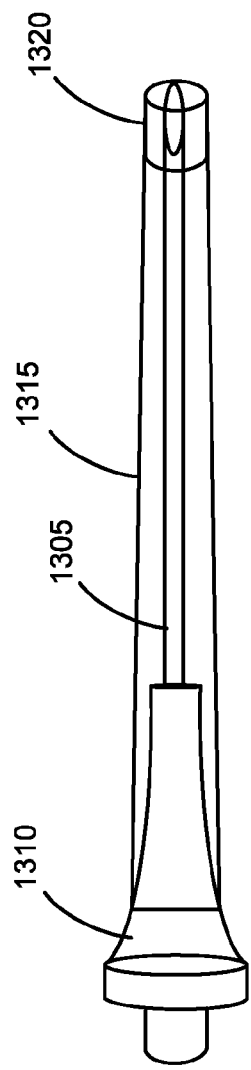
FIGS. 13A and 13B show exemplary 19G filter needles, each covered by a thin 0.0005 inch thick sleeve with a contamination prevention tip (CPT) made of silicone.
Figure 13B:
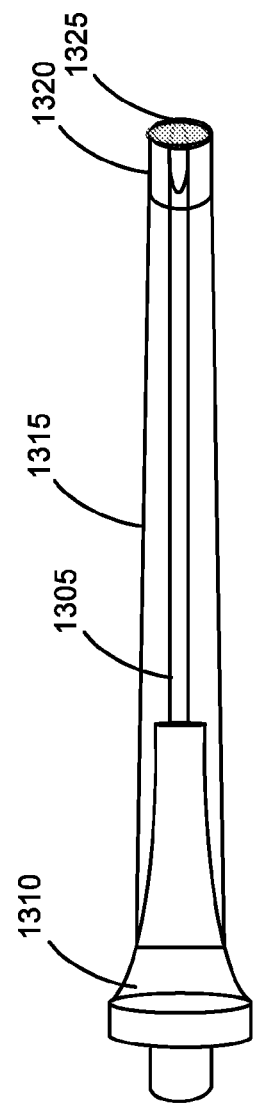
Figure 14:
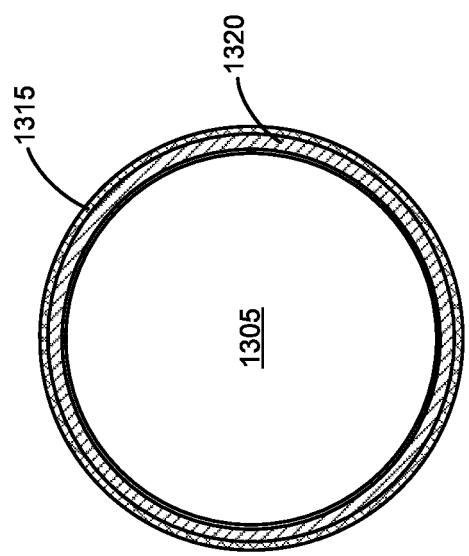
FIG. 14 shows an alternate view of a 19G with the CPT.

FIGS. 13A and 13B show 19G needles 1305, each attached to a needle hub 1310 and having a thin protective sleeve 1315 with a contamination prevention tip (CPT) 1320. FIG. 14 shows a cross-sectional view of the tip of the needle 1305 of either FIG. 13A or 13B, surrounded by the protective sleeve 1315 and the contamination prevention tip.

The contamination prevention tip (CPT) 1320 serves multiple functions. The CPT 1320 helps to ensure the fine protective sleeve 1315 does not contaminate the needle 1305 by folding in on itself during insertion. A fine protective sleeve 1315 can have a thickness of about 0.0005 inches. The CPT 1320 lowers the likelihood that the protective sleeve 1315 will enter the injection site along with the needle 1305. The contamination prevention tip 1320 can be attached to the outside of the protective sleeve or the inside of the protective sleeve. FIGS. 13A and 13B show the CPT 1320 affixed to the inside of the protective sleeve 1315 surrounding each needle 1305. Silicone can be used to make the contamination prevention tip 1320. The CPT 1320 can also be made of the same material as the protective sleeve 1315. In general, the contamination prevention tip 1320 is considerably thicker than the sleeve 1315. The contamination prevention tip 1320 can have a thickness of around 0.01 inches (0.254 mm), or more. This value is generally thicker than the protective sleeve 1315. Typically, the CPT 1320 is on or near the needle 1305 tip and has a length of around 0.15 inches for a 19G, 1½ inch filter needle, although it can be larger, but not much smaller. The length of the contamination prevention tip can vary depending on the size of the needle being protected as well as the application. FIG. 13B shows a protective sleeve 1315 covering a needle 1305 with a contamination prevention tip 1320 that has a thin covering material 1325 closing the sleeve 1315 and enclosing the needle 1305. The thin covering 1325 can include a polyethylene film of 0.0005 inches in thickness or the like.

In some implementations, a needle can be protected by a thin polymer sleeve that is attached the needle hub and extends to the needle tip, where a contamination prevention tip is attached. The thin polymer sleeve can have a thickness of 0.0020 inches or less, such as 0.0010 inches or less, such as 0.0008 inches or less, including 0.0005 inches or less. The thin polymer sleeve protecting a needle from the hub to the needle tip can have a thickness of 0.0005 inches in some implementations. The contamination prevention tip can include a polymer, silicone, an elastomeric material, nylon, a polyethylene, a ceramic, or any combination thereof. The thickness of the contamination prevention tip can vary according to the needle size and application. For example, the contamination prevention tip for use with a 19G, 1½ inch filter needle, such as can be used to extract fluid from a vial, can range from 0.005 inches to 0.1 inches, such as from 0.010 inches to 0.080 inches, including 0.010 inches to 0.050 inches. In some implementations, the thickness of the contamination prevention tip can be 0.010 inches on average. In some implementations, the thickness of the contamination prevention tip can be 0.035 inches or more. The length of the contamination prevention tip can range from 1/16 the length of the needle from tip to hub to ½ the length of the needle. Additionally, the length of the contamination prevention tip can range from 1/12 the length of the needle to ⅓ the length of the needle. Alternatively, the length of the contamination prevention tip can range from 0.075 inches to 0.500 inches, such as 0.090 inches to 0.200 inches, including 0.100 inches to 0.150 inches. In some implementations, the length of the contamination prevention tip is 0.150 inches. The inner diameter (ID) of the contamination prevention tip can range from 0.040 inches to 0.080 inches, such as from 0.050 inches to 0.070 inches. In some implementations, the ID of the contamination prevention tip is 0.065 inches on average. The outer diameter (OD) of the contamination prevention tip can range from 0.050 inches to 0.090 inches, including from 0.070 inches to 0.080 inches. The outer diameter of the contamination prevention tip can be 0.075 inches in some implementations. As mentioned herein above, the dimensions of the contamination prevention tip can vary based upon application and needle size.

Figure 15:
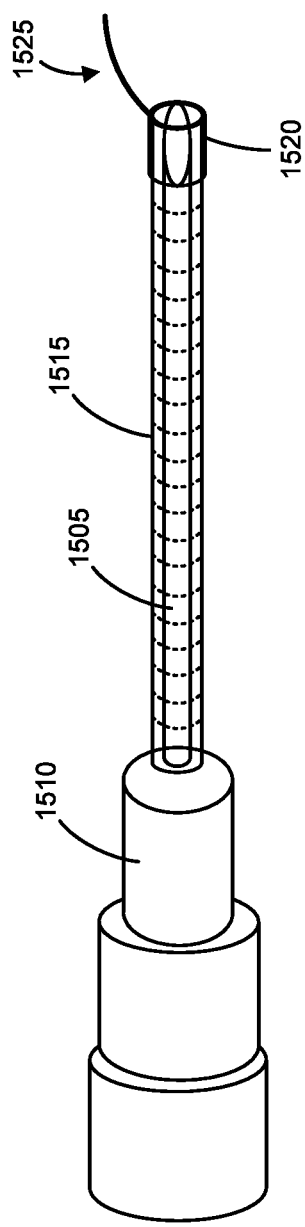
FIGS. 15 and 16 show a 33G needle with an offset marking attachment that allows a user to more precisely determine the distance of the needle from an anatomical structure.
Figure 16:
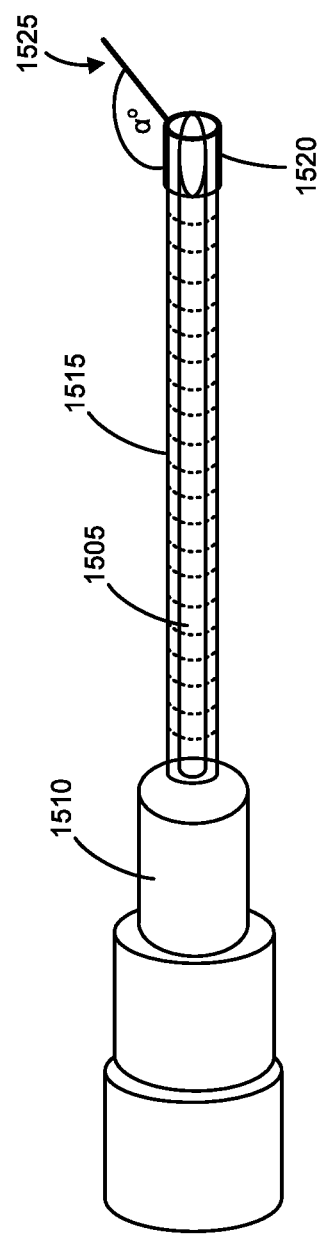

FIGS. 15 and 16 each show a needle 1505 attached to a hub 1510 with a protective sleeve 1515 and a contamination prevention tip (CPT) 1520 with an offset marker 1525 attached. The offset marker 1525 allows precise placement of the needle tip within the protective sleeve 1515 relative to another point. The offset marker 1525 can be made from any suitable material that is suitably rigid or resilient, as well as not irritating to sensitive areas, such as the eye. A suitable material for the offset marker 1525 can be a piece of silicone tubing. An offset marker 1525 can have markings like a ruler at regular intervals, such as 1, 2 3 and 4 mm, so as to allow precise insertion of the needle with respect to an anatomical structure or other feature. The offset marker 1525 can be cylindrical, elliptical, square, rectangular, or any other geometric configuration that aids is precisely locating an injection site with respect to another feature. Alternatively, the offset can be achieved by increasing the thickness of the contamination prevention tip or the thicker portion near a needle tip (606 in FIG. 6). Increasing the thickness of thickened portion of the sleeve near the needle tip can increase the outer diameter of that part of the sleeve. A sufficiently large radius on the tip portion of a protective sleeve can help a user gauge the distance from a structure or feature and the needle tip.

The angle between the axial direction of the offset maker 1525 and the longitudinal axis of the needle 1505 ($\alpha$ in FIG. 16) can range from 20° to 180°, depending on the use and desired offset. Additionally, the angle between the axial direction of the offset maker 1525 and the longitudinal axis of the needle 1505 with respect to the longitudinal axis of the needle 1505 ($\alpha$ in FIG. 16) can range from 75° to 160°. Alternatively, the angle $\alpha$ can be approximately a 135° as shown in FIG. 16. The higher and lower values at the extremes of these ranges for $\alpha$ can facilitate the insertion of a needle with an offset marker into the rigid protective caps that typically surround commercially available needles when they are shipped. These angles also allow the offset marker 1525 to contact a surface, such as an eye, and then deform as the needle 1505 approaches the surface. FIG. 15 shows the device with an offset marker 1525 with a slight curve, and FIG. 16 with a straight marker. Using a higher angle $\alpha$ can minimize the contact between the offset marker and the hard shell that covers and prevents contamination of the GID prior to use.

Figure 17:
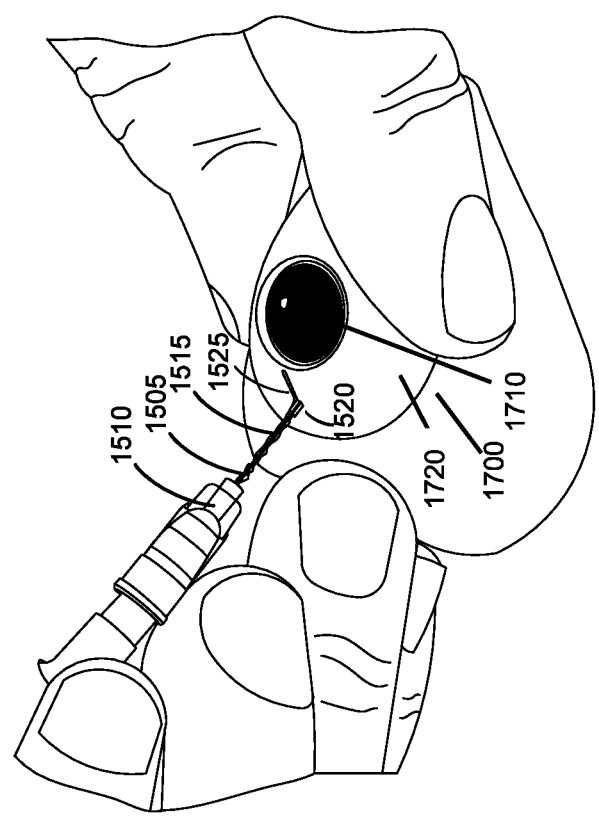
FIG. 17 illustrates a needle with a sleeve, a contamination prevention tip, and an offset marker in use with a simulated eye.

FIG. 17 illustrates a needle 1505 with a sleeve 1515 attached to a hub 1510 on an injection device. At the distal end of the sleeve 1515 is a contamination prevention tip 1520 that has an offset marker 1525. The offset marker 1525 is shown as a protrusion of tubing. FIG. 17 shows the needle before an injection is made, pressed against a simulated eye 1700 that has a corneal portion 1710 and a sclera portion 1720. A user, such as a doctor or other medical practitioner, who knows the length of the offset marker 1525 can align the distal end of the needle 1505 a known distance from the edge of the junction of the cornea and the sclera 1710 into the sclera portion 1720. The user can align the offset marker 1525 to be perpendicular or nearly perpendicular to a tangent to the edge of the corneal portion. This can be useful for intravitreal injections in which a user, or clinician, will want to avoid certain structures in the eye behind the sclera, such as the retina. Alternatively, if an injection site is to be in another organ, precision of site location can be achieved by knowing the location of a reference structure and the length of an offset marker 1525.

Figure 18:
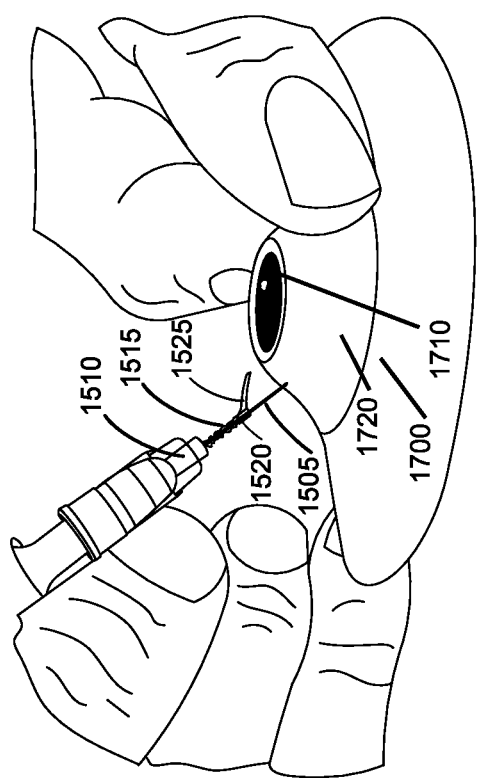
FIG. 18 illustrates a needle with a sleeve, a contamination prevention tip, and an offset marker in after inserting the needle into the simulated eye of FIG. 17.

FIG. 18 illustrates a needle 1505 with a sleeve 1515 similar to the one in FIG. 17. The needle 1505 and sleeve 1515 are shown after the needle 1505 has been inserted into the simulated eye 1700 in the sclera portion 1720. The sleeve 1515 can be seen to be collapsed below the hub 1510 and above the contamination prevention tip 1520. At the end of the contamination prevention tip 1520 is the offset marker 1525, which helped the user determine the distance from the edge of the cornea portion 1710. The offset marker 1525 can be seen to be angled towards the simulated eye 1700. The initial angle between the needle 1505 covered by the sleeve 1515 and the offset marker 1525 ($\alpha$ in FIG. 16), can be different from the angle after an injection is administered. Conversely, the connection point between the offset marker 1525 and the contamination prevention tip 1520 can be resilient, and the initial and post-injection angle ($\alpha$ in FIG. 16) can be the same, such as within 5 or less degrees.

EXAMPLES

The following experimental study number 1 illustrates that the use of the component and sleeves (shown in FIGS. 3-7) can prevent contamination of the needles (whether such needles are needles used for drawing up the fluid from a container/vial and/or injection needles). The use of the vial serves as a model for the eye, as it has a rubber stopper that simulates the scleral tissue in the eye allowing the needle to be inserted but stopping the sleeve, and can have fluid inside it similar to an eye that can become contaminated. The second exemplary experimental study illustrates the forces used in systems with and without protective sleeves. Exemplary experimental study number 3 illustrates comparisons of both the time needed to accomplish an injection and the relative comfort of a patient when using a needle with a protective sleeve, or a guarded injection device (GID), versus when using a conventional needle.

Exemplary Experimental Study No. 1

Study Methods and Procedures:

Simulated eyes were used with needles with and without protective sleeves to assess the amount of contamination protection provided by systems using protective sleeves. In order to simulate a model eye, vials of ranibizumab (Lucentis®, Genentech, San Francisco, Calif.) and aflibercept (Eylea®, Regeneron, Terrytown, N.Y.) were fully emptied of contents and filled with 2 cc of sterile thioglycollate medium (BD™, Franklin Lakes, N.J.). Six different scenarios were assessed using this model: a contaminated 19 gauge needle with and without a guard, a contaminated 33 gauge needle with and without a guard, and an uncontaminated 19 and 33 gauge needle each without a guard as controls. The injection devices (IJDVs) were autoclaved for 20 minutes at 270° F. in a M7 Speedclave® (Midmark, Versailles, Ohio) in a validated medical device pouch to maintain sterility prior to intentional contamination of the needle. All contaminated needles, with or without the shielding device, were contaminated with saliva from one of the investigators which was applied equally across all devices using a saliva covered swab. After insertion of the needle from the IJDV with a contaminated exterior shield into the vial and whirling it around in the culture media, the vial was placed in an incubator at 33-35° C. for up to six weeks, though it was checked for growth at 48 and 72 hours. A similar test was done with the standard needles, one in which the sides of the needles were contaminated with the same spit and another in which the needles were not contaminated as a control. Two vials from each manufacturer were tested for each experimental arm. In the event of growth in the vials, samples were sent to a microbiology lab for identification of the infecting organisms.

Results:

Both vials of ranibizumab and of aflibercept into which saliva-contaminated standard 19G filter needles were inserted developed heavy microbial growth at 72 hours. Neither of the vials of ranibizumab and of aflibercept into which the saliva-contaminated shielded 19 G filter needles were inserted showed any growth at 72 hours. Similarly, both of the vials of ranibizumab and of aflibercept into which a saliva-contaminated standard 33 G needle was inserted showed heavy growth at 48 hours. Neither of the vials of ranibizumabor of aflibercept into which saliva-contaminated shielded 33G needles were inserted showed any growth at 48 hours. The control group of uncontaminated, standard needles failed to result in contamination following vial insertion into the culture media. All vials found to be uncontaminated at 72 hours remained that way throughout the full observation period of 6 weeks. One vial from each contaminated group was sent to microbiology. Results from the microbiological assessment determined the contaminating microbes to be *Streptococcus* Viridian groups in all cases. In summary, vial contamination with the investigational device was absent as compared to vials in which a standard needle was used (p<0.01, Chi Square). TABLE 2 illustrates the results of the above study.

TABLE 2

Experimental Results

| Needle | Sleeve | Bottle | Growth | Time |
|---|---|---|---|---|
| 33G | No Sleeve No contamination | Generic | No Growth | 72 hours |
| 33G | Dumbbell | Lucentis ® | No Growth | 72 hours |
| 33G | Dumbbell | Lucentis ® | No Growth | 72 hours |
| 33G | No Sleeve | Lucentis ® | Heavy Growth | 72 hours |
| 33G | No Sleeve | Lucentis ® | Heavy Growth | 72 hours |
| 33G | Dumbbell | Eylea ® | No Growth | 72 hours |
| 33G | Dumbbell | Eylea ® | No Growth | 72 hours |
| 33G | No Sleeve | Eylea ® | Heavy Growth | 72 hours |
| 33G | No Sleeve | Eylea ® | Heavy Growth | 72 hours |
| 33G | No Sleeve No contamination | Generic | No Growth | 72 hours |
| 19 G filter | 0.0005 inch | Lucentis ® | No Growth | 72 hours |
| 19 G filter | 0.0005 inch | Lucentis ® | No Growth | 72 hours |
| 19 G filter | No Sleeve | Lucentis ® | Heavy Growth | 72 hours |
| 19 G filter | No Sleeve | Lucentis ® | Heavy Growth | 72 hours |
| 19 G filter | 0.0005 inch | Eylea ® | No Growth | 72 hours |
| 19 G filter | 0.0005 inch | Eylea ® | No Growth | 72 hours |
| 19 G filter | No Sleeve | Eylea ® | Heavy Growth | 72 hours |
| 19 G filter | No Sleeve | Eylea ® | Heavy Growth | 72 hours |

Some embodiments, the exemplary injection device can reduce a risk of contamination of commonly used medications for intravitreal (IV) injections. While the incidence of endophthalmitis following IV injections is low, the outcome tends to be poor. The injection devices, systems, and methods described herein can help to reduce the risk of infection from saliva, while allowing physicians to communicate more with patients during IV injections without the need for a mask.

Exemplary Experimental Study No. 2

Study Methods and Procedures:

Comparisons of the force needed to penetrate an insertion site using bare needles and needles with protective sleeves were made. 33G needles were tested with or without a silicone needle guard sleeve composed of medical grade silicone tubing (ID 0.01 inches and OD 0.015 inches) with either a 1.5 or a 2.5 mm silicone tubing (ID 0.020 inches and OD 0.037 inches) contamination prevention tip, and 19G needles were tested with or without a 0.0005 inch wall thickness needle guard composed of polyethylene. The test was done by recording the amount of force needed for the 19G or 33G needle to enter a material similar in consistence to the human sclera. The test parameters included advancing the needle into the material at a rate of 100 microns per second. The needle was advanced until about 60% to 70% of the collapsible portion of the sleeve was collapsed. For needles with a contamination prevention tip (CPT), the CPT was not included in the measurement of the collapsible portion of the sleeve. As described hereinabove, the sclera-simulating material is a proprietary test media developed by InvenGen (InvenGen, Reading, Pa.) that is used by ophthalmic OEM device manufacturers for its high signal-to-noise properties. Five needles, with or without a protective sleeve, were tested in each experimental arm (see Table 3A). Five 19G filter needles without a protective sleeve and five similar needles with protective sleeves having a 0.0005 inch thickness were tested. Additionally, a set of 19G needles, each with a 0.0005 inch thickness sleeve and a contamination prevention tip near the needle tip were tested and compared (see Table 3B). The contamination prevention tips (CPT) were pieces of silicone tubing that were 0.065 inches in inner diameter, 0.075 inches in outer diameter, and 0.150 inches in length.

Additional force testing was performed using both using a butterfly needle device and the covered needle that came with the butterfly needle for insertion into a vacutainer tube. The needle with an opaque gray covering that came with the butterfly needle was tested for insertion into a vacutainer with or without the shielding device composed of what appears to be medical grade silicone tubing on the back end of a butterfly needle 1001. This grey silicone cover for use with the vacutainer that comes with the butterfly needle set has an outer diameter of 0.090 inches and a wall thickness of 0.026 inches. This test was repeated using the 23G needle on the front end of the butterfly device with or without a 0.0005 inch wall thickness polyethylene sleeve 1002 (FIG. 10). Again, five needles, with or without the sheath, were tested in each experimental arm (see Table 4).

Results:

For an unshielded 33G needle alone the amount of gram-force (gf) needed was 59+/−3.4 gf, whereas for the shielded 33G needle with the 2.5 mm contamination prevention tip (CPT) was 72.8+/−2.7 gf. Though the difference between the two is statistically significant (p<0.05, Student's T-test), the amount of added force of needed as a percentage is acceptable. As a percentage, the guarded injection device (GID) required about 23% more force in the test model, far less than the 50% limitation. The total amount of additional force required for the 33G with the 2.5 mm CPT was 13.8. The numbers for the 33G with the 1.5 mm CPT were similar. The unshielded 19G needles required an amount of 259.9+/−13.1 gf, whereas for the shielded 19G needles it was 238.4+/−15.7 (gf). It is interesting that the force required was less for the shielded version than the needle alone, and that this difference is statistically significant by a Student's T-test (p=0.046). The tests of the 19G with the contamination prevention tip (CPT) revealed little additional force was needed to perform an injection with the contamination prevention tip. The average amount of force needed with the GID and the CPT was 266.26 grams force versus 269.78 grams force without the tip. The difference between the results for these two types of configurations was not statistically significant.

The tests using the grey silicone tip of the back of the needle that is used to penetrate a vacutainer found the additional force required for the grey vacutainer needle cover of 204 gram-force was over 100 gf and also 60% greater than that of the unshielded butterfly needle (540.22+/−24.24 gf vs 336.5+/−14.28 gf), which exceeds the preferred amount of force defined for the device described hereinabove (see Table 4A). The tests using the 23G needle on the butterfly device 1002 (FIG. 10) showed an almost identical force requirement with or without the sleeve, with the shielded device requiring 184+/−23.3 gf. This is 0.4%, less force than the unshielded device, which required 184.75+/−14.41 gf (Table 4B). The grey silicone cover used to penetrate vacutainers is also thicker than the ideal materials for most of the embodiments presented herein, with an internal diameter of 0.038 inches and an outer diameter of 0.090 inches for a wall thickness of 0.026 inches. The needle covered by the grey silicone cover 1001 is 20G with an outer diameter of 0.035 inches. The total distance between the cover over the vacutainer needle and the needle on both sides of the needle is 0.047 inches, which is significantly higher than the total value of 0.015 inches for the 33G silicone version used for intravitreal injections.

TABLE 3A

Experimental results from 33G injection and 19G filter needle force tests with and without a needle guard.

| Test No | Sample/gauge (-thickness of sheath) | Maximum Load (gf) |
|---|---|---|
| | Needle with Shielding sheath | |
| 1 | 33G-2.5 mm | 69.9 |
| 2 | 33G-2.5 mm | 74.8 |
| 3 | 33G-2.5 mm | 70.7 |
| 4 | 33G-2.5 mm | 76.4 |
| 5 | 33G-2.5 mm | 72.2 |
| | Mean | 72.8 |
| | Standard Deviation | 2.7 |
| 1 | 33G-1.5 mm | 75 |
| 2 | 33G-1.5 mm | 77.9 |
| 3 | 33G-1.5 mm | 69.8 |
| 4 | 33G-1.5 mm | 73 |
| 5 | 33G-1.5 mm | 68.3 |
| | Mean | 72.8 |
| | Standard Deviation | 3.9 |
| 1 | 19G-0.0005 in | 217.3 |
| 2 | 19G-0.0005 in | 234.0 |
| 3 | 19G-0.0005 in | 233.7 |
| 4 | 19G-0.0005 in | 250.7 |
| 5 | 19G-0.0005 in | 256.5 |
| | Mean | 238.4 |
| | Standard Deviation | 15.5 |
| | Needle without Shielding sheath | |
| 1 | 33G Needle-no sheath | 62.0 |
| 2 | 33G Needle-no sheath | 58.4 |
| 3 | 33G Needle-no sheath | 61.4 |
| 4 | 33G Needle-no sheath | 59.5 |
| 5 | 33G Needle-no sheath | 53.5 |
| | Mean | 59.0 |
| | Standard Deviation | 3.4 |
| 1 | 19G Needle-no sheath | 238.4 |
| 2 | 19G Needle-no sheath | 260.8 |
| 3 | 19G Needle-no sheath | 274.2 |
| 4 | 19G Needle-no sheath | 263.4 |
| 5 | 19G Needle-no sheath | 262.7 |
| | Mean | 259.9 |
| | Standard Deviation | 13.1 |
| | Difference in force needed for 33G | 23.47% |
| | Difference in force needed for 19G | 8.26% |

TABLE 3B

Experimental results from 19G filter needle force tests using a configuration with a needle guard with a contamination preventing tip on a 0.0005 inch sleeve compared and a bare needle configuration

| Sample Number | 19G filter Needle with 0.0005-inch Thick Protective Sleeve Force (grams f) | 19G filter Needle without Protective Sleeve Force (grams f) |
|---|---|---|
| 1 | 273.31 | 297.15 |
| 2 | 260.52 | 263.07 |
| 3 | 241.77 | 254.42 |
| 4 | 280.63 | 279.21 |
| 5 | 275.06 | 255.04 |
| Mean | 266.26 | 269.78 |
| Std. Deviation | 15.54 | 18.28 |

TABLE 4

Experimental results from force tests using (A) the needle which is covered with a grey silicone tip on the back end of a butterfly needle which is designed to be inserted into a vacutainer and which was inserted into the force testing material that is similar in consistence to the human sclera with or without a thick grey needle guard 1001 or (B) the 23 G needle on the front end of the butterfly device 1002 inserted into a enter a material similar in consistence to the human sclera with or without a 0.0005 inch wall thickness sleeve.

| Test Number | Shielded needle Maximum Load (gf) | Standard, unshielded needle Maximum Load (gf) |
|---|---|---|
| A. Test using grey tip on BD Vacutainer Safety Lock Blood Collection Set | | |
| 1 | 576.5 | 330 |
| 2 | 531.3 | 339.5 |
| 3 | 508.8 | 354.5 |
| 4 | 541.7 | 316.3 |
| 5 | 542.8 | 342.2 |
| Mean | 540.22 | 336.5 |
| Standard Deviation | 24.45 | 14.28 |
| Difference in force needed | 60.5% | |
| B. Test using 23 G tip on BD Vacutainer Safety Lock Blood Collection Set | | |
| 1 | 167.4 | 179.1 |
| 2 | 179.3 | 179.5 |
| 3 | 174.2 | 206.9 |
| 4 | 174.3 | 168.7 |
| 5 | 225.0 | 129.5 |
| Mean | 124 | 184.74 |
| Standard Deviation | 23.30 | 14.41 |
| Difference in force needed | 0.4% | |

Sample penetration performance is normally distributed.

Exemplary Experimental Study No. 3

Study Methods and Procedures:

The study was designed to evaluate a total of 500 consenting patients (or 1000 eyes). As of Aug. 9, 2012, 31 patients had consented, though five were lost to follow-up after completing the questionnaire immediately following the procedure. Consented patients received injections of the same volume of a vascular endothelial growth factor inhibitor (i.e. ranabizumab, bevacizmab, or aflibercept) in each eye on the same day. One eye was injected with a 30 gauge needle (with the aid of a speculum) and the other eye was injected with the guarded injection device (GID) that had a 33 gauge needle (without the aid of a speculum). While different drugs were allowed in each eye, the majority of the patients received the same medication in each eye. The eye that received the injection from the standard 30 gauge (S30G) needle was determined randomly (by coin toss).

A stopwatch measured the amount of time needed for each injection. For standard needle injections, the timer was started when the physician picked up the speculum from the counter. The timer was stopped when the injection was completed, the needle was disposed of in the medical waste container, and the speculum was placed back on the counter. For procedures that involved the GID, the timer was started when the physician picked up the GID, and the timer was stopped when the injection was completed and the GID was placed in the waste disposal container.

Patients received anesthetic for the injections in one of two ways: sub-conjunctival injection or topical anesthetic. Both methods are common in retinal clinics and which method used varies by doctor. In this study, the method of applying anesthetic depended on the comfort of the physician and patient with the method. However, the study protocol was restricted to using similar anesthetic methods in both eyes of each patient, so each patient served as his or her own control.

Following each session of injections, the patient was asked to fill out a short questionnaire regarding the comfort levels of the two injection devices, both during and immediately following the injection. Also, the study investigators contacted all test subjects by phone 24 hours after the injection to assess any post-injection pain on the evening of the injection or the day after, giving a total of 4 time points for comfort analysis. Pain scores were scaled from 0 to 4, with 0 being no pain, 1 being mild pain, 2 being moderate pain, 3 being severe pain, and 4 being extremely severe pain.

Figure 19:
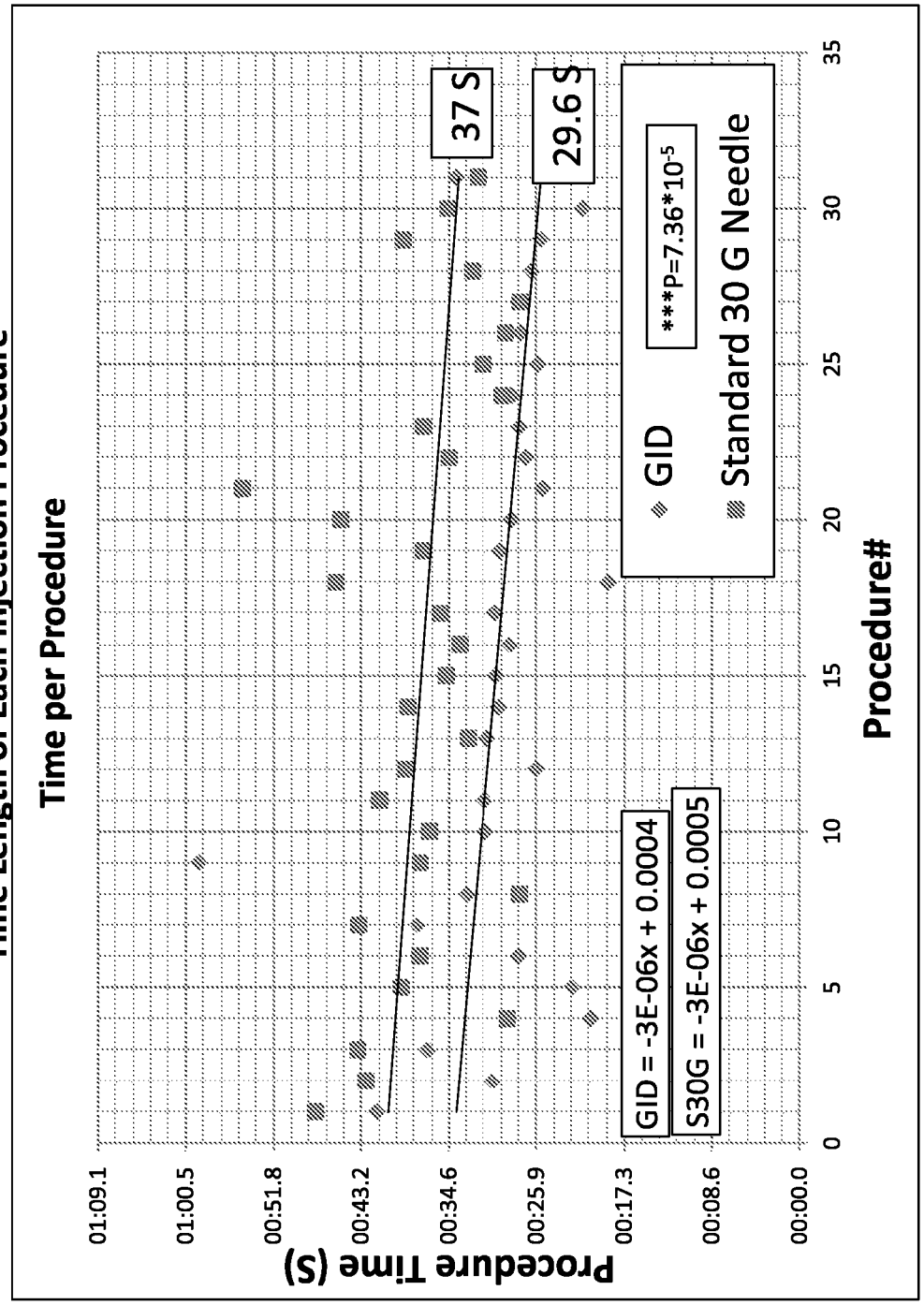
FIG. 19 shows a graph of the length of time for each injection procedure.

Procedure Time Results:

Initial results showed the average time needed to perform an IV (intravitreal) injection using the GID with a 33G needle was found to be significantly shorter when compared to an S30G needle used with a lid speculum. The procedure using the GID took an average time of 29.6+/−7.3 seconds (s) while the standard needle took 37+/−6.4 (s) (FIG. 19). Thus, intravitreal injections were completed about 25% faster when using the GID (p=7.36*10$^{-5}$, Student's T-test). This time advantage for the GID procedure over the standard procedure did not include the time needed to obtain a sterile eye lid speculum prior to the injection, the time to clean the speculum following the injection, nor the time to package and sterilize the eye lid speculum in a steam sterilizer (i.e. autoclave) after cleaning.

Figure 20:
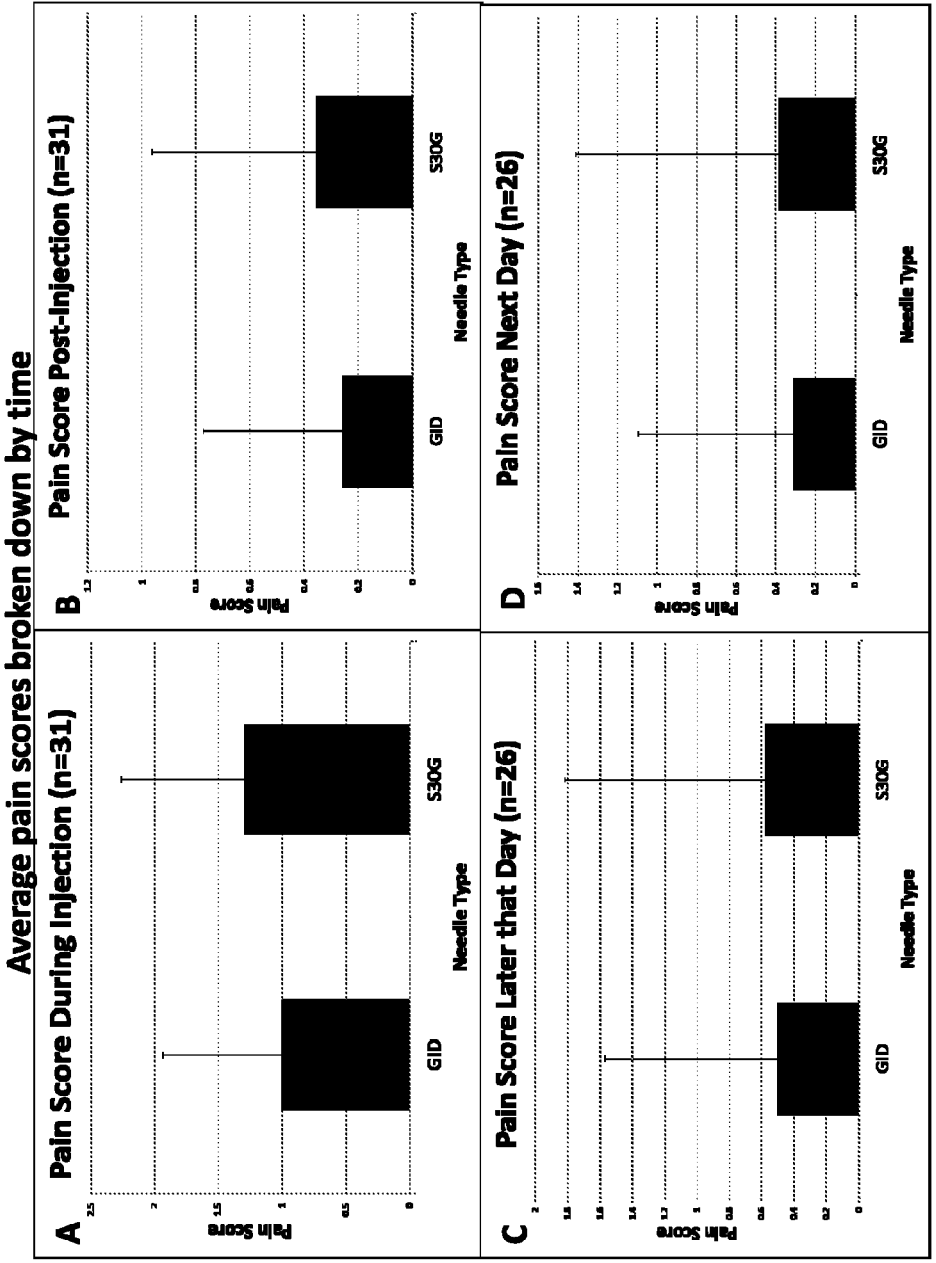
FIG. 20 shows the average pain scores broken down by time.

Comfort Analysis Results:

The results from the comfort analysis showed clear trends that seemed to indicate that the procedures that used GID were more comfortable, though the difference was not statistically significant, as can be seen in FIG. 20. Further experiments may show a statistically significant difference. The average pain score for procedures that used the GID to administer the injection was 1+/−0.93, while the average pain score for procedures that used a standard 30G needle was 1.29+/−0.97 (FIG. 20A; p=0.23, Student's T-test). The average pain score immediately following the injection procedure was 0.25+/−0.51 from the GID and 0.35+/−0.61 from the standard needle (FIG. 20B; p=0.5, Student's T-test). The average pain score later that day was 0.5+/−1.07 from the GID and 0.57+/−1.24 from the standard needle (FIG. 20C; p=0.8, St-test). The average pain score 24 hours following the injection procedure was 0.31+/−0.79 from the GID and 0.38+/−1.02 from the standard needle (FIG. 20D; p=0.76, Student's T-test). Thus, at all time points the GID was rated more comfortable.

During all but the first injection in the study, patients were filmed digitally during the injection to see if the GID protected the needle from contamination during the injection. In 4 of the first 31 patients injected, review of the films show the eyelids in contact with the GID. Despite this contact, there have been no intraocular infections during the study in patients that received an injection using the GID. In the study it was not possible to compare what would have happened if the GID had not been present following the contact, as this would have been unethical. It is known that the incidence of endophthalmitis is low, and it is possible none of these patients would have been infected if the GID had not been used and the lids had contacted the needle, at some point most likely an infection would have resulted from the contamination. Exemplary Experiment #1 demonstrated that the GID can reduce the incidence of needle contamination. As needle contamination can be presumed to be the cause of an eye infection, and this experiment showed that the GID did protect the needle from contamination during the injections in patients (humans), this study demonstrated that a method of intraocular medication injection using a needle with a protective sleeve around it could reduce the risk of needle contamination during intraocular injections in humans.

The films also showed that for a successful injection, the needle did not have to be inserted maximally into the eye. In other words, a successful injection could be made with only partial collapse of the protective sleeve. In general, inserting the tip around 3 mm or more into the eye was sufficient to perform a successful injection into the vitreous cavity. Although the needle tip could be inserted less than 3 mm and still result in administering drug to the vitreous cavity, inserting the needle tip 3 mm or more into a patient's eye was felt to increase the likelihood that the drugs consistently reached the vitreous cavity.

Thus, the results from the clinical trial to date demonstrate that the GID reduces the time needed (FIG. 19) for an injection and increases the overall comfort level (FIG. 20). Digital films taken during the use of the GID also demonstrated how both the device and a method of injecting using a needle with a shield over it can protect the needle from contamination during intravitreal injections in humans.

FIG. 19 shows the time length of each injection procedure. Each eye injection was timed using a stopwatch and plotted on a graph in the order they were performed. Trend lines were calculated and displayed. n=31. FIG. 20 shows the average pain scores broken down by time. Pain scores were calculated (A) during the injection procedure (n=31), (B) immediately following the procedure (n=31), (C) later that evening (n=26), and (D) the next day (n=26).

Example embodiments of the methods and components of the present invention disclosure have been described herein. As noted elsewhere, these example embodiments have been described for illustrative purposes only, and are not limiting. Other embodiments are possible and are covered by the invention disclosure. Such embodiments will be apparent to persons skilled in the relevant art(s) based on the teachings contained herein. Thus, the breadth and scope of the present invention disclosure should not be limited by any of the above-described exemplary embodiments, but should be defined only in accordance with the following claims and their equivalents.

What is claimed is:

1. A device, comprising:
a non-rigid, non-resilient, collapsible sleeve having a proximal end coupled to a distal end of an injection device, the injection device including a needle coupled to the distal end of the injection device, wherein the needle has a distal end;
the collapsible sleeve, in an original shape, extends from the proximal end to the distal end of the needle, and covers the needle before penetration of the needle into an insertion site and covers the needle at least partially during penetration of the needle into the insertion site, the collapsible sleeve at least partially permanently collapsing by folding upon penetration of the needle through a distal end of the collapsible sleeve and into the insertion site, such that the collapsible sleeve does not return to the original shape, wherein a force of less than 100 gram-force is required to collapse the sleeve, wherein a length of the collapsible sleeve is at least one of the following: longer than a length of the needle, shorter than the length of the needle, and same as the length of the needle.

2. The device according to claim 1, wherein the sleeve does not penetrate the insertion site.

3. The device according to claim 1, wherein the force required to collapse the sleeve is determined by calculating the amount of force needed to insert the needle when using the needle with the sleeve and subtracting the amount of force needed to insert the needle in a similar manner without the sleeve.

4. The device according to claim 1, wherein the force required to collapse the sleeve is measured by advancing a needle with the sleeve into a simulated human sclera at a rate of 100 microns per second until up to 70% of the portion of the sleeve that is capable of collapse has collapsed.

5. The device according to claim 4, wherein the force required to collapse the sleeve is measured by advancing a needle with the sleeve into a simulated human sclera at a rate of 100 microns per second until up to 30% of the portion of the sleeve that is capable of collapse has collapsed.

6. The device according to claim 4, wherein the needle comprises a tip at its distal end, further wherein the sleeve comprises a contamination prevention tip located at the distal end of the sleeve surrounding needle tip, the contamination prevention tip not being part of the portion of the sleeve that is capable of collapse.

7. The device according to claim 1, wherein the force required to collapse the sleeve ranges from 0.0001 gram-force to 100 gram-force.

8. The device according to claim 7, wherein the force required to collapse the sleeve ranges from 0.0001 gram-force to 75 gram-force.

9. The device according to claim 1, wherein the sleeve is clear or transparent.

10. The device according to claim 1, wherein the sleeve comprises color pigments so as to allow easier visualization of the sleeve, further wherein the sleeve is sufficiently transparent to allow visualization of the needle.

11. The device according to claim 1, wherein the needle has an outside diameter and the sleeve has an inside diameter such that the difference between the needle's outer diameter and sleeve's inside diameter is between 0.05 and 6 times an outer diameter of the needle.

12. The device according to claim 11, wherein the difference between the needle's outer diameter and sleeve's inside diameter is based upon a smallest inside diameter of the sleeve and an average outer diameter of the needle.

13. The device according to claim 1, wherein the sleeve has an enlarged portion of the sleeve adjacent to a needle tip of the needle.

14. The device according to claim 13, wherein the enlarged portion of the sleeve is achieved by attaching a piece of tubing that is larger than the sleeve covering the needle only at a portion of the sleeve adjacent to the needle tip.

15. The device according to claim 13, wherein the enlarged portion of the sleeve is achieved by attaching a piece of tubing inside the sleeve that covers the needle only at a portion of the sleeve adjacent to the needle tip.

16. The device according to claim 13, wherein the sleeve has a thickness of 0.0020 inches or less and the enlarged portion of the sleeve has a thickness of 0.0100 inches or more.

17. The device according to claim 13, wherein the enlarged portion of the sleeve has a length less than or equal to ½ the length of the sleeve.

18. The device according to claim 1, wherein the sleeve has a baffle configuration that allows for a controlled collapse.

19. The device according to claim 1, wherein the sleeve includes at least one of the following: an antibacterial medication, an antibacterial agent, an anti-microbial medication, an anti-microbial agent, and any combination thereof.

20. The device according to claim 19, wherein a medication includes at least one of the following: an antibiotic, an antiviral medication, an antifungal medication, an antiprotozoal, an anti-inflammatory drug, and any combination thereof.

21. The device according to claim 19, wherein at least one of the antibacterial agent and the anti-microbial agent includes at least one of the following: a colloidal silver, any other suitable form of silver, a colloidal gold, an antimicrobial chemical, any other substance that kills or inhibits the growth of microorganisms including bacteria, fungi, or protozoans, and any combination thereof.

22. The device according to claim 1, further comprising an offset marker at the distal end of the sleeve.

23. The device according to claim 22, wherein the offset marker comprises hash marks, variations in coloring, variations in size or any combination thereof that indicate increments of distance.

24. The device according to claim 22, wherein the offset marker is straight, curved, looped, a ring, a rectangle, or any combination thereof.

25. The device according to claim 22, wherein the offset marker is angled forward, backward or at a 90° from the needle axis.

26. The device according to claim 22, wherein the offset marker is rigid or resilient.

27. The device according to claim 22, wherein the offset marker is flexible.

28. The device according to claim 1, wherein the sleeve includes at least one of the following: a plastic, a silicone, a medical grade silicone, Polyethelene (PE), TetraFluorEthylene-Perfluorpropylene (FEP), PerFluoroAlkoxy (PFA), and any combination thereof.

29. The device according to claim 1, wherein an additional force needed to collapse the sleeve is defined as the difference between:
a force needed to penetrate a first injection site using the needle with the sleeve; and
a force needed to penetrate a second injection site using the needle without the sleeve;

over the force needed to penetrate the first injection site using the needle without the sleeve expressed as a percentage, further wherein the first and second injection sites comprise similar tissue or material, and wherein the additional force needed to collapse the sleeve is less than 50%.

30. The device according to claim 29, wherein the additional force needed to collapse the sleeve is less than 25%.

31. The device according to claim 29, wherein forces needed to derive the additional force needed to collapse the sleeve comprise the force needed to penetrate the first injection site using the needle with the sleeve and the force needed to penetrate the second injection site using the needle without the sleeve, and the forces needed to derive the additional force needed to collapse the sleeve are measured by advancing the needle with and without the sleeve into a simulated human sclera at a rate of 100 microns per second.

* * * * *